United States Patent
Verma et al.

(10) Patent No.: US 9,408,863 B2
(45) Date of Patent: Aug. 9, 2016

(54) 5'-SUBSTITUTED NUCLEOSIDE ANALOGS AND METHODS OF USE THEREOF FOR THE TREATMENT OF VIRAL DISEASES

(75) Inventors: Vishal A. Verma, Jersey City, NJ (US); Ashok Arasappan, Bridgewater, NJ (US); F. George Njoroge, Carmel, IN (US); Kevin X. Chen, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 224 days.

(21) Appl. No.: 14/232,536

(22) PCT Filed: Jul. 10, 2012

(86) PCT No.: PCT/US2012/046038
§ 371 (c)(1),
(2), (4) Date: Apr. 11, 2014

(87) PCT Pub. No.: WO2013/009737
PCT Pub. Date: Jan. 17, 2013

(65) Prior Publication Data
US 2014/0221304 A1    Aug. 7, 2014

Related U.S. Application Data

(60) Provisional application No. 61/507,364, filed on Jul. 13, 2011.

(51) Int. Cl.
| | | |
|---|---|---|
| A01N 43/04 | (2006.01) |
| A61K 31/70 | (2006.01) |
| C07H 19/20 | (2006.01) |
| C07H 19/10 | (2006.01) |
| C07H 19/04 | (2006.01) |
| C07H 19/048 | (2006.01) |
| A61K 31/7056 | (2006.01) |
| A01N 37/46 | (2006.01) |
| C07H 19/06 | (2006.01) |
| C07H 19/16 | (2006.01) |
| A61K 31/341 | (2006.01) |
| A61K 31/4196 | (2006.01) |
| A61K 31/7068 | (2006.01) |
| A61K 31/7072 | (2006.01) |
| A61K 31/7076 | (2006.01) |
| A61K 31/708 | (2006.01) |
| A61K 45/06 | (2006.01) |

(52) U.S. Cl.
CPC ............ *A61K 31/7056* (2013.01); *A01N 37/46* (2013.01); *A61K 31/341* (2013.01); *A61K 31/4196* (2013.01); *A61K 31/708* (2013.01); *A61K 31/7068* (2013.01); *A61K 31/7072* (2013.01); *A61K 31/7076* (2013.01); *A61K 45/06* (2013.01); *C07H 19/06* (2013.01); *C07H 19/10* (2013.01); *C07H 19/16* (2013.01); *C07H 19/20* (2013.01)

(58) Field of Classification Search
CPC . A01N 37/46; A61K 31/7072; A61K 31/341; A61K 31/4196; A61K 31/7076; A61K 31/708; A61K 45/06; A61K 31/7068; A61K 31/7056; A61K 2300/00; C07H 19/16; C07H 19/06; C07H 19/20; C07H 19/10
See application file for complete search history.

(56) References Cited

U.S. PATENT DOCUMENTS

| | | |
|---|---|---|
| 3,480,613 A | 11/1969 | Walton |
| 1,187,824 A | 4/1970 | Walton |
| 4,211,773 A | 7/1980 | Lopez et al. |
| 4,666,892 A | 5/1987 | Fox et al. |
| 4,808,614 A | 2/1989 | Hertel |
| 5,672,594 A | 9/1997 | Weis et al. |
| 5,837,852 A | 11/1998 | Chung et al. |
| 5,977,061 A | 11/1999 | Holy et al. |
| 6,063,628 A | 5/2000 | Loeb et al. |

(Continued)

FOREIGN PATENT DOCUMENTS

| | | |
|---|---|---|
| FR | 1581628 | 9/1969 |
| WO | 9318051 | 9/1993 |

(Continued)

OTHER PUBLICATIONS

Mehta, et al., Biochemistry, 1976, pp. 4329-4333,vol. 15, No. 19.
Beers, et al., "The Merck Manual of Diagnosis and Therapy", 1999, Seventeenth Edition, pp. 377-386, 1132, 1280.
Chu, et al. "9-Deazaadenosine—A New Potent antitumor Agent", Biochemical Pharmacology, 1984, vol. 33, pp. 1229-1234.
Clark, et al., "Synthesis and Antiviral Activity of 2'-Deoxy-2'-Fluoro-2'-C-Methyl Purine Nucleosides As Inhibitors of Hepatitits C Virus RNA Replication", Bioorganic & Medicinal Chemistry Letters, 2006, vol. 16, pp. 1712-1715.
Dee Nord, et al., "Inhibition of Orotidylate Decarboxylase by 4(5H)-Oxo-1-B-D-Ribofuranosylpyrazolo[3,4-d]    Pyrimidine-3-Thiocarboxamide (APR-TC) in B Lymphoblasts", Biochemical Pharmacology, 1988, vol. 37, pp. 4697-4705.

(Continued)

*Primary Examiner* — Lawrence E Crane
(74) *Attorney, Agent, or Firm* — Jeffrey P. Bergman; Catherine D. Fitch

(57) ABSTRACT

The present invention relates to 5'-Substituted Nucleoside Analogs of Formula (I): and pharmaceutically acceptable salts thereof, wherein B, X, Z, $R^1$, $R^2$, $R^3$ and $R^{3'}$ are as defined herein. The present invention also relates to compositions comprising at least one 5'-Substituted Nucleoside Analog, and methods of using the 5'-Substituted Nucleoside Analogs for treating or preventing HCV infection in a patient.

(I)

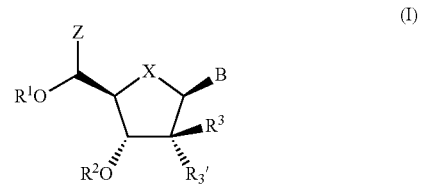

12 Claims, No Drawings

(56) References Cited

U.S. PATENT DOCUMENTS

| | | | |
|---|---|---|---|
| 6,110,901 | A | 8/2000 | Gluzman et al. |
| 6,348,587 | B1 | 2/2002 | Schinazi et al. |
| 6,777,395 | B2 | 8/2004 | Bhat et al. |
| 6,784,161 | B2 | 8/2004 | Ismaili et al. |
| 6,812,219 | B2 | 11/2004 | LaColla et al. |
| 6,914,054 | B2 | 7/2005 | Sommadossi et al. |
| 7,101,861 | B2 | 9/2006 | Sommadossi et al. |
| 7,105,499 | B2 | 9/2006 | Carroll et al. |
| 7,112,600 | B1 | 9/2006 | Hashimoto et al. |
| 7,125,855 | B2 | 10/2006 | Bhat et al. |
| 7,157,441 | B2 | 1/2007 | Sommadossi et al. |
| 7,169,766 | B2 | 1/2007 | Sommadossi et al. |
| 7,202,224 | B2 | 4/2007 | Eldrup et al. |
| 7,405,204 | B2 | 7/2008 | Roberts et al. |
| 7,429,572 | B2 | 9/2008 | Clark |
| 7,973,013 | B2 | 7/2011 | Cho et al. |
| 8,575,119 | B2 * | 11/2013 | Wang .......... A61K 38/212 514/43 |
| 8,772,474 | B2 * | 7/2014 | Beigelman ......... A61K 31/14 536/26.11 |
| 8,871,737 | B2 * | 10/2014 | Smith ............... C07H 19/06 514/47 |
| 2002/0019363 | A1 | 2/2002 | Ismaili et al. |
| 2002/0053096 | A1 | 5/2002 | Hirschberg et al. |
| 2002/0055483 | A1 | 5/2002 | Watanabe et al. |
| 2002/0147160 | A1 | 10/2002 | Bhat et al. |
| 2002/0198171 | A1 | 12/2002 | Schinazi et al. |
| 2003/0007946 | A1 | 1/2003 | Narang et al. |
| 2003/0013089 | A1 | 1/2003 | Fisher et al. |
| 2003/0050229 | A1 | 3/2003 | Sommadossi et al. |
| 2003/0060400 | A1 | 3/2003 | LaColla et al. |
| 2004/0072788 | A1 | 4/2004 | Bhat et al. |
| 2005/0272676 | A1 | 12/2005 | Bhat et al. |
| 2006/0205686 | A1 | 9/2006 | Bhat et al. |
| 2006/0241064 | A1 | 10/2006 | Roberts et al. |
| 2007/0042988 | A1 | 2/2007 | Klumpp et al. |
| 2007/0259832 | A1 | 11/2007 | Cook et al. |
| 2007/0265222 | A1 | 11/2007 | MacCoss et al. |
| 2007/0275912 | A1 | 11/2007 | Bhat et al. |
| 2010/0021425 | A1 | 1/2010 | Butler et al. |
| 2010/0104532 | A1 | 4/2010 | Chen et al. |
| 2010/0297079 | A1 | 11/2010 | Almond et al. |
| 2010/0298257 | A1 | 11/2010 | Ross et al. |
| 2010/0316594 | A1 | 12/2010 | Sommadossi et al. |
| 2012/0009147 | A1 | 1/2012 | Cho et al. |
| 2012/0237480 | A1 | 9/2012 | Or et al. |
| 2014/0128339 | A1 | 5/2014 | Girijavallabhan et al. |
| 2014/0154211 | A1 | 6/2014 | Girijavallabhan et al. |
| 2014/0235567 | A1 | 8/2014 | Verma et al. |

FOREIGN PATENT DOCUMENTS

| | | | |
|---|---|---|---|
| WO | 9405687 | | 3/1994 |
| WO | 9816184 | A2 | 4/1998 |
| WO | 9943691 | | 9/1999 |
| WO | 0132153 | | 5/2001 |
| WO | 0160315 | | 8/2001 |
| WO | 0179246 | | 10/2001 |
| WO | 0190121 | | 11/2001 |
| WO | 0218404 | | 3/2002 |
| WO | 0232920 | A2 | 4/2002 |
| WO | 0248165 | A2 | 6/2002 |
| WO | 02069903 | A2 | 9/2002 |
| WO | 02094289 | A1 | 11/2002 |
| WO | 02100354 | A2 | 12/2002 |
| WO | 02100415 | A2 | 12/2002 |
| WO | 03000200 | A2 | 1/2003 |
| WO | 03000713 | A1 | 1/2003 |
| WO | 03015798 | A1 | 2/2003 |
| WO | 03026589 | A2 | 4/2003 |
| WO | 03026675 | A1 | 4/2003 |
| WO | 03051881 | | 6/2003 |
| WO | 03051896 | | 6/2003 |
| WO | 03051897 | | 6/2003 |
| WO | 03051898 | | 6/2003 |
| WO | 03051899 | | 6/2003 |
| WO | 03062255 | | 7/2003 |
| WO | 03093290 | A2 | 11/2003 |
| WO | 2004003000 | A2 | 1/2004 |
| WO | 2004080989 | | 9/2004 |
| WO | 2009061781 | A1 | 5/2009 |
| WO | 2010108140 | A1 | 9/2010 |
| WO | 2010135520 | A1 | 11/2010 |
| WO | 0192282 | | 12/2011 |
| WO | 2012040126 | A1 | 3/2012 |

OTHER PUBLICATIONS

Eldrup, et al., "Structure-Activity Relationship of Purine Ribonucleosides for Inhibition of Hepatitis C Virus RNA-Dependent RNA Polymerase", Journal of Medicinal Chemistry, 2004, vol. 47, pp. 2283-2295.

Flockhart, et al., "ATP Analog Specificity of gAMP-Dependent Protein Kinase, cGMP-Dependent Protein Kinase, and Phosphorylase Kinase", European Journal of Biochemistry, 1984, vol. 140, pp. 289-295.

Gupta, et al., "Genetic and Biochemical Studies on Mutants of CHO Cells Resistant to 7-Deazapurine Nucleosides: Differences in the Mechanisms of Action of Toyocamycin and Tubercidin", Biochemical and Biophysical Research Communications, 1984, vol. 120, pp. 88-95.

Hoofnagle, "Therapy of Viral Hepatitis", Digest, 1998, vol. 59, pp. 563-578.

Olsen, et al., A 7-Deaza-Adenosine Analog Is a Potent and Selective Inhibitor of Hepatitis C Virus Replication With Excellent Pharmacokinetic Properties, Antimicrobial Agents and Chemotherapy, 2004, vol. 48, pp. 3944-3953.

Ono, et al., "Oligodeoxynucleotides Containing 7-Deazaadenine: Synthesis and Recognition of Restriction Endonucleases", Eleventh Symposium on Nucleic Acids Chemistry, Tokyo, Japan, Nov. 1-2, 1983, published in Nucleic Acids Symposium Series No. 12, pp. 67-70.

Seela, et al., "7-(B-D-Arabinofuranosyl)-2,4-Dichlor-7H-Pyrrolo[2,3-d]Pyrimidin—Synthese, Selektiver Halogenaustausch und ElnfluB Glyconischer Schutzgruppen Auf Die Reaktivität des Aglycons", Liebigs Annalen der Chemie, 1984, pp. 722-733.

Bailly et al., "Treatment of HCV Liver disease by Recombinant Interferon Alpha", Nephrology Dialysis Transplantation, 1996, vol. 11, Suppl. 4, pp. 56-57.

Abbruzzese, James L., et al., Phase I trial of 1-(2-deoxy-2-'fluoro-1-beta-D-arabinofuranosyl)-5-methyluracil (FMAU) terminated by severe neurologic toxicity, Investigational New Drugs, 1989, vol. 7, pp. 195-201.

Chu, Chung, K., et al., "Use of 2'-Fluoro-5-Methyl-B-L-Arabinofuranosyluracil As a Novel Antiviral Agent for Hepatitis B Virus and Epstein-Barr Virus", Antimicrobial Agents and Chemotherapy, 1995, vol. 39, No. 4., pp. 979-981.

Harada, Kazuho, et al., "Nucleosides, 139, Synthesis and Antictomegalovirus and Antiherpes Simplex Virus Activity of 5-Modified Analogues of 2'-Fluoroarabinosylpyrimidine Nucleosides", J. Med. Chem. 198, vol. 30, pp. 226-229, (1987).

Merluzzi, V.J., et al., "Comparison of 2'-Fluoro-Arabinosyl Pyrimidine Nucleosides and 1-B-D-Arabinofuranosylcytosine on Immunological Parameters In Vitro", Int. J. Immunopharmacology, 1983, vol. 5, No. 5, pp. 421-425.

AN 1990:135032 for Savochkina, et al, Molekulyarnaya Biologiya (Moscow), 1989, vol. 23, No. 6, pp. 1347-1356.

* cited by examiner

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer

<400> SEQUENCE: 1
atggacaggc gccctga                                                  17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                               20

<210> SEQ ID NO 3
<211> LENGTH: 17
<212> TYPE: DNA
<213> ORGANISM: Artificial Sequence
<220> FEATURE:
<223> OTHER INFORMATION: FAM labeled probe

<400> SEQUENCE: 3
cacgccatgc gctgcgg                                                  17
```

5'-SUBSTITUTED NUCLEOSIDE ANALOGS AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US2012/046038, filed Jul. 10, 2012, which claims priority to U.S. Provisional Application No. 61/507364, filed Jul. 13, 2011. Each of the aforementioned PCT and priority applications is incorporated by reference in its entirety.

REFERENCE TO SEQUENCE LISTING SUBMITTED ELECTRONICALLY

The sequence listing of the present application is being submitted electronically via EFS-Web as an ASCII formatted sequence listing with a file name "23084USPCT-SEQTXT-2014JAN13.txt", creation date of Jan. 13, 2014 and a size of 1 KB. This sequence listing submitted via EFS-Web is part of the specification and is herein incorporated by reference in its entirety.

FIELD OF THE INVENTION

The present invention relates to 5'-Substituted Nucleoside Analogs, compositions comprising at least one 5'-Substituted Nucleoside Analog, and methods of using the 5'-Substituted Nucleoside Analogs for treating or preventing HCV infection in a patient.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, of the U.S. Center for Disease Control. Of the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy,* 11:79-96 (2000); H. Rosen, et al., "Hepatitis C virus: current understanding and prospects for future therapies," *Molecular Medicine Today,* 5:393-399 (1999); D. Moradpour, et al., "Current and evolving therapies for hepatitis C," *European J. Gastroenterol. Hepatol.,* 11:1189-1202 (1999); R. Bartenschlager, "Candidate Targets for Hepatitis C Virus-Specific Antiviral Therapy," *Intervirology,* 40:378-393 (1997); G. M. Lauer and B. D. Walker, "Hepatitis C Virus Infection," *N. Engl. J. Med.,* 345:41-52 (2001); B. W. Dymock, "Emerging therapies for hepatitis C virus infection," *Emerging Drugs,* 6:13-42 (2001); and C. Crabb, "Hard-Won Advances Spark Excitement about Hepatitis C," *Science,* 06-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology,* 29:1227-1235 (1999) and V. Lohmann, et al., "Biochemical and Kinetic Analyses of NS5B RNA-Dependent RNA Polymerase of the Hepatitis C Virus," *Virology,* 249:108-118 (1998)]. Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in M. P. Walker et al., "Promising candidates for the treatment of chronic hepatitis C," *Expert Opin. Invest. Drugs,* 12:1269-1280 (2003) and in P. Hoffmann et al., "Recent patents on experimental therapy for hepatitis C virus infection (1999-2002)," *Expert Opin. Ther. Patents,"* 13:1707-1723 (2003). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.,* 47:2283-2295 (2004).

There is a continuing need for structurally diverse nucleoside derivatives as inhibitors of HCV polymerase as therapeutic approaches for HCV therapy. This invention responds to that need.

SUMMARY OF THE INVENTION

In one aspect, the present invention provides Compounds of Formula (I):

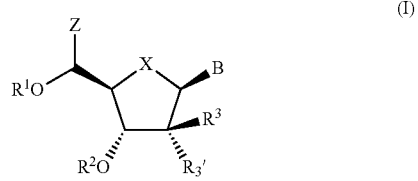

(I)

and pharmaceutically acceptable salts thereof,
wherein:
X is O, S or $CH_2$;
Z is $C_1$-$C_6$ alkyl, $C_2$-$C_6$ alkenyl, $C_2$-$C_6$ alkynyl, —($C_1$-$C_3$ alkylene)$_m$-($C_3$-$C_7$ cycloalkyl), —($C_1$-$C_3$ alkylene)$_m$-$C_6$-$C_{10}$ aryl, —($C_1$-$C_3$ alkylene)$_m$-(4 to 7-membered heterocycloalkyl group), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —OR$^{20}$, —SR$^{20}$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —C(O)OR$^{20}$, —C(O)N(R$^{20}$)$_2$ and —NHC(O)R$^{20}$;

B is a natural or non-natural purine or pyrimidine base, or B is selected from one of the following groups:

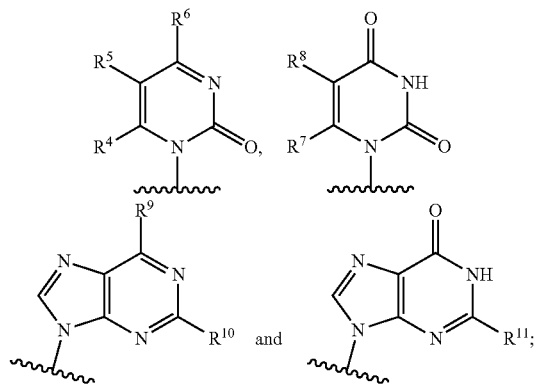

R$^1$ is H, —C(O)—$C_{1-6}$ alkyl,

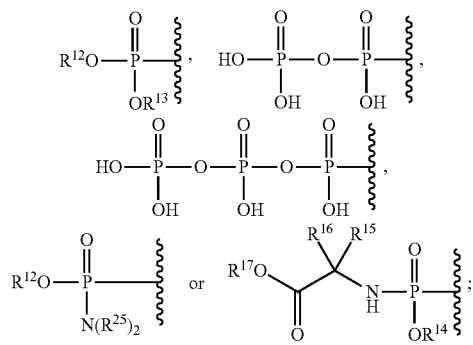

R$^2$ is H or —C(O)—$C_{1-6}$ alkyl, or R$^1$ and R$^2$ join to form a group having the formula:

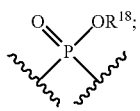

R$^3$ is —OH, halo, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl or $C_3$-$C_7$ cycloalkyl;

R$^{3'}$ is —OH, halo, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl or $C_3$-$C_7$ cycloalkyl, such that R$^3$ and R$^{3'}$ cannot both be —OH;

R$^4$, R$^5$, R$^7$ and R$^8$ are each independently H, $C_1$-$C_6$ alkyl, $C_1$-$C_6$ haloalkyl, $C_1$-$C_6$ hydroxyalkyl, halo, —OR$^{20}$, —SR$^{20}$ or —N(R$^{20}$)$_2$;

R$^6$, R$^9$, R$^{10}$, R$^{11}$ are each independently selected from H, $C_1$-$C_6$ alkyl, $C_2$-$C_6$ alkenyl, $C_2$-$C_6$ alkynyl, $C_3$-$C_7$ cycloalkyl, 5- or 6-membered monocyclic heteroaryl, 9- or 10-membered bicyclic heteroaryl, halo, —OR$^{20}$, —SR$^{20}$, —S(O)R$^{20}$, —S(O)$^2$R$^{20}$, S(O)$_2$N(R$^{20}$)$_2$, —NHC(O)OR$^{20}$, —NHC(O)N(R$^{20}$)$_2$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —NH($C_1$-$C_6$ alkylene)-(5- or 6-membered monocyclic heteroaryl), —NH($C_1$-$C_6$ alkylene)-(9- or 10-membered bicyclic heteroaryl), —C(O)R$^{20}$, —C(O)OR$^{20}$, —C(O)N(R$^{20}$)$_2$ and —NHC(O)R$^{20}$, wherein said $C_2$-$C_6$ alkenyl group and said $C_2$-$C_6$ alkynyl group can be optionally substituted with a halo group;

R$^{12}$ is H or —($C_1$-$C_6$ alkylene)-T-R$^{21}$;

R$^{13}$ is H or —($C_1$-$C_6$ alkylene)-T-R$^{21}$, or R$^{12}$ and R$^{13}$ can join to form a $C_2$-$C_4$ alkylene group between the oxygen atoms that R$^{12}$ and R$^{13}$ are attached to, wherein said $C_2$-$C_4$ alkylene group is substituted with at least one $C_6$-$C_{10}$ aryl group;

R$^{14}$ is H, $C_6$-$C_{10}$ aryl, 5- or 6-membered monocyclic heteroaryl or 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with R$^{22}$;

R$^{15}$ is H, $C_1$-$C_6$ alkyl, $C_3$-$C_7$ cycloalkyl, phenyl or benzyl, wherein said $C_1$-$C_6$ alkyl can be optionally substituted with a group selected from halo, —OR$^{20}$, —SR$^{20}$, guanidino, —N(R$^{20}$)$_2$, —C(O)OR$^{20}$, —C(O)N(R$^{20}$)$_2$, NHC(O)R$^{20}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —OR$^{20}$;

R$^{16}$ is H, $C_1$-$C_6$ alkyl, $C_3$-$C_7$ cycloalkyl, phenyl or benzyl, wherein said $C_1$-$C_6$ alkyl can be optionally substituted with a group selected from halo, —OR$^{20}$, —SR$^{20}$, guanidino, —N(R$^{20}$)$_2$, —C(O)OR$^{20}$, —C(O)N(R$^{20}$)$_2$, —NHC(O)R$^{20}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —OR$^{20}$;

R$^{17}$ is H, $C_1$-$C_{20}$ alkyl, $C_2$-$C_{20}$ alkenyl, —($C_1$-$C_3$ alkylene)$_m$-$C_3$-$C_7$ cycloalkyl, —($C_1$-$C_3$ alkylene)$_m$-$C_6$-$C_{10}$ aryl or adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —OR$^{20}$, —C(O)OR$^{20}$, CN, NO$_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —N(R$^{20}$)$_2$, —C(O)N(R$^{20}$)$_2$, —SR$^{20}$, —S(O)R$^{20}$, —S(O)$_2$R$^{20}$, —S(O)$_2$N(R$^{20}$)$_2$, —NHC(O)R$^{20}$, —NHC(O)OR$^{20}$ and —NHC(O)N(R$^{20}$)$_2$ and;

R$^{18}$ is H, $C_1$-$C_6$ alkyl, $C_3$-$C_7$ cycloalkyl, —($C_1$-$C_3$ alkylene)$_m$-$C_6$-$C_{10}$ aryl, 5- or 6-membered monocyclic heteroaryl or 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —OR$^{20}$, —SR$^{20}$, $C_1$-$C_6$ haloalkyl, $C_1$-$C_6$ hydroxyalkyl, —O—($C_1$-$C_6$ haloalkyl), —CN, —NO$_2$, —N(R$^{20}$)$_2$, —C(O)OR$^{20}$, —C(O)N(R$^{20}$)$_2$ and —NHC(O)R$^{20}$;

each occurrence of R$^{20}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with $R^{26}$;

each occurrence of $R^{21}$ is independently H, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_7$ cycloalkyl, $C_3$-$C_7$ cycloalkenyl, 5- or 6-membered monocyclic heteroaryl, 9- or 10-membered bicyclic heteroaryl, —$OR^{20}$, —O—($C_1$-$C_6$ haloalkyl) or —N($R^{20}$)$_2$, wherein said $C_2$-$C_6$ alkenyl group, said $C_2$-$C_6$ alkynyl group, said $C_3$-$C_7$ cycloalkyl group, said $C_3$-$C_7$ cycloalkenyl group, said $C_6$-$C_{10}$ aryl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —N($R^{20}$)$_2$, —C(O)$R^{20}$, —C(O)$OR^{20}$, —C(O)N($R^{20}$)$_2$ and —NHC(O)$R^{20}$;

$R^{22}$ represents from one to five substituent groups, each independently selected from $C_1$-$C_6$ alkyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —N($R^{20}$)$_2$, —C(O)$OR^{20}$, —C(O)N($R^{20}$)$_2$ and —NHC(O)$R^{20}$, or any two $R^{22}$ groups on adjacent ring carbon atoms can combine to form —O—$R^{23}$—O—;

$R^{23}$ is —[C($R^{24}$)$_2$]$_n$—;

each occurrence of $R^{24}$ is independently H or $C_1$-$C_6$ alkyl;

each occurrence of $R^{25}$ is independently H, $C_1$-$C_6$ alkyl, $C_2$-$C_6$ alkenyl, $C_2$-$C_6$ alkynyl, $C_3$-$C_7$ cycloalkyl, —($C_1$-$C_3$ alkylene)$_m$-($C_6$-$C_{10}$ aryl), 4 to 7-membered heterocycloalkyl, 5- or 6-membered monocyclic heteroaryl or 9- or 10-membered bicyclic heteroaryl, wherein said $C_1$-$C_6$ alkyl group, said $C_2$-$C_6$ alkenyl group, said $C_2$-$C_6$ alkynyl group, said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with $R^{26}$; or two $R^{25}$ groups, together with the common nitrogen atom to which they are attached, join to form a 4- to 7-membered heterocycloalkyl group;

$R^{26}$ represents from one to five substituent groups, each independently selected from $C_1$-$C_6$ alkyl, $C_2$-$C_6$ alkenyl, $C_2$-$C_6$ alkynyl, halo, —$OR^{27}$, —$SR^{27}$, $C_1$-$C_6$ haloalkyl, $C_1$-$C_6$ hydroxyalkyl, —O—($C_1$-$C_6$ haloalkyl), —CN, —$NO_2$, —N($R^{27}$)$_2$, —C(O)$OR^{27}$, —C(O)N($R^{27}$)$_2$ and —NHC(O)$R^{27}$;

each occurrence of $R^{27}$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

each occurrence of T is independently —S—, —O—, —SC(O)—, —SC(S)—, —OC(O)— and —OC(S)—;

each occurrence of m is independently 0 or 1; and each occurrence of n is independently 1 or 2.

The Compounds of Formula (I) (also referred to herein as the "5'-Substituted Nucleoside Analogs") and pharmaceutically acceptable salts thereof can be useful, for example, for inhibiting HCV viral replication or replicon activity, and for treating or preventing HCV infection in a patient. Without being bound by any specific theory, it is believed that the 5'-Substituted Nucleoside Analogs inhibit HCV viral replication by inhibiting HCV NS5B.

Accordingly, the present invention provides methods for treating or preventing HCV infection in a patient, comprising administering to the patient an effective amount of at least one 5'-Substituted Nucleoside Analog.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to 5'-Substituted Nucleoside Analogs, compositions comprising at least one 5'-Substituted Nucleoside Analog, and methods of using the 5'-Substituted Nucleoside Analogs for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of 5'-Substituted Nucleoside Analog and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms.

Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

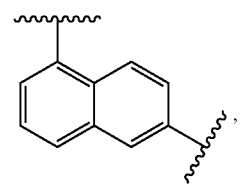 [SMILES: *c1ccc2c(*)cccc2c1]

is understood to represent both:

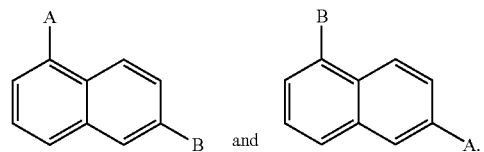

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

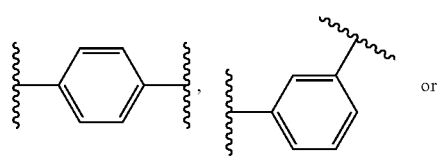

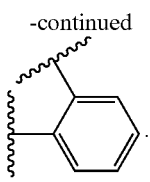

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

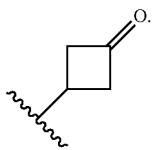 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

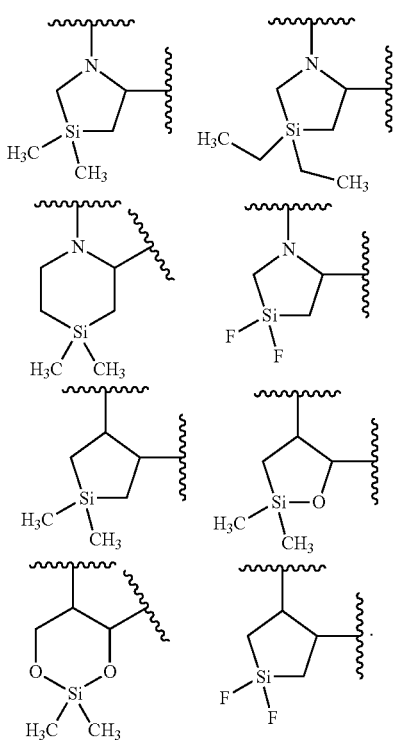

A ring carbon atom of a heterocycloalkyl group may be functionalized as a carbonyl group. An illustrative example of such a heterocycloalkyl group is:

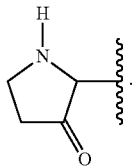 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "natural or non-natural purine or pyrimidine base" includes, but is not limited to, adenine, $N^{6\text{-}alkylpurines}$, $N^{6\text{-}acylpurines}$ (wherein acyl is C(O)(alkyl, aryl, alkylaryl, or arylalkyl), $N^{6\text{-}benzylpurine}$, $N^{6\text{-}halopurine}$, $N^{6\text{-}vinylpurine}$, $N^{6\text{-}acetylenic}$ purine, $N^{6\text{-}acyl}$ purine, $N^{6\text{-}hydroxyalkyl}$ purine, $N^{6\text{-}thioalkyl}$ purine, $N^{2\text{-}alkylpurines}$, $N^{2\text{-}alkyl\text{-}6\text{-}thiopurines}$, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^{5\text{-}alkylpyrimidines}$, $C^{5\text{-}benzylpyrimidines}$, $C^{5\text{-}halopyrimidines}$, $C^{5\text{-}vinylpyrimidine}$, $C^{5\text{-}acetylenic}$ pyrimidine, $C^{5\text{-}acyl}$ pyrimidine, $C^{5\text{-}hydroxyalkyl}$ purine, $C^{5\text{-}amidopyrimidine}$, $C^{5\text{-}cyanopyrimidine}$, $C^{5\text{-}nitropyrimidine}$, $C^{5\text{-}aminopyrimidine}$, $N^{2\text{-}alkylpurines}$, $N^{2\text{-}alkyl\text{-}6\text{-}thiopurines}$, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary ordesired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

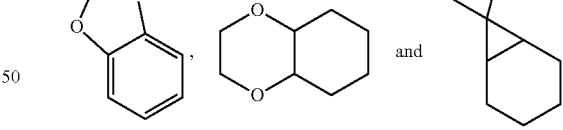

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently C$_1$-C$_6$ alkyl, phenyl or a 3 to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include —CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^6$, $R^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a 5'-Substituted Nucleoside Analog or a pharmaceutically acceptable salt of the compound. The transformation may occur by various mechanisms (e.g., by metabolic or chemical processes), such as, for example, through hydrolysis in blood.

For example, if a 5'-Substituted Nucleoside Analog or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a 5'-Substituted Nucleoside Analog contains an alcohol functional group, a prodrug can be formed by the replacement of one or more of the hydrogen atoms of the alcohol groups with a group such as, for example, $(C_1-C_6)$ alkanoyloxymethyl, 1-(($C_1-C_6$)alkanoyloxy)ethyl, 1-methyl-1-(($C_1-C_6$)alkanoyloxy)ethyl, ($C_1-C_6$)alkoxycarbonyloxymethyl, N—($C_1-C_6$)alkoxycarbonylaminomethyl, succinoyl, ($C_1-C_6$)alkanoyl, α-amino($C_1-C_4$)alkyl, α-amino($C_1-C_4$) alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other non-limiting example of alcohol-derived prodrugs include —P(O) $(OH)_2$; —P(O)(—O—$C_1-C_6$alkyl)$_2$; —P(O)(—NH-(α-aminoacyl group))(—O-aryl); —P(O)(—O—($C_1-C_6$ alkylene)-S-acyl)(—NH-arylalkyl); any cyclic phosphate ester that forms a bridge between two ribose hydroxyl groups, such as:

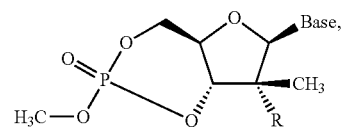

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

If a 5'-Substituted Nucleoside Analog incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N- or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$ alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$) acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 5'-Substituted Nucleoside Analogs can form salts which are also within the scope of this invention. Reference to a 5'-Substituted Nucleoside Analog herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 5'-Substituted Nucleoside Analog contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 5'-Substituted Nucleoside Analog with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quartemized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the 5'-Substituted Nucleoside Analogs may be atropisomers (e.g., substituted biaryls) and are considered as part of this invention. Enantiomers can also be directly separated using chiral chromatographic techniques.

It is also possible that the 5'-Substituted Nucleoside Analogs may exist in different tautomeric forms, and all such forms are embraced within the scope of the invention.

For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 5'-Substituted Nucleoside Analog incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the 5'-Substituted Nucleoside Analogs, and of the salts, solvates, hydrates, esters and prodrugs of the 5'-Substituted Nucleoside Analogs, are intended to be included in the present invention.

The following abbreviations are used below and have the following meanings: Ac is acetyl or —C(O)CH$_3$, AcOH is acetic acid; t-BuMgCl is tert-butyl magnesium chloride; Dess-Martin Periodinane is 1,1,1-triacetoxy-1,1-dihydro-1,2-benziodoxol-3(1H)-one; DIAD is diisopropylazodicarboxylate; DMAP is dimethylaminopyridine; DMP is 2,2-dimethoxypropane; EtOAc is ethyl acetate; HPLC is high performance liquid chromatography; MeMgBr is methylmagnesium bromide; TBSCl is tert-butyldimethylsilyl chloride; TEMPO is 2,2,6,6-tetramethylpiperidine-N-oxide; TFA is trifluoroacetic acid; THF is tetrahydrofuran; TMSOTf is trimethylsilyl trifluoromethanesulfonate; TsOH is p-toluenesulfonic acid.

The Compounds of Formula (I)

The present invention provides 5'-Substituted Nucleoside Analogs of Formula (I):

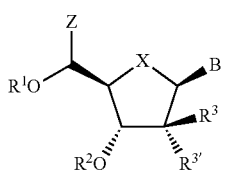
(I)

and pharmaceutically acceptable salts thereof, wherein B, X, Z, R$^1$, R$^2$, R$^3$ and R$^{3'}$ are defined above for the Compounds of Formula (I).

In one embodiment, X is O.
In another embodiment, X is S.
In another embodiment, X is CH$_2$.
In one embodiment, Z is C$_1$-C$_6$ alkyl.
In another embodiment, Z is C$_3$-C$_7$ cycloalkyl.
In another embodiment, Z is C$_6$-C$_{10}$ aryl.
In another embodiment, Z is methyl.

In one embodiment, R$^1$ is H or

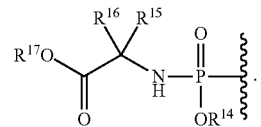

In another embodiment, R$^1$ is:

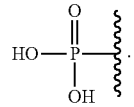

In another embodiment, R$^1$ is:

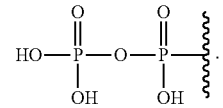

In another embodiment, R$^1$ is:

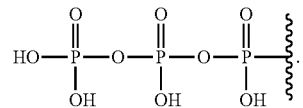

In still another embodiment, R$^1$ is:

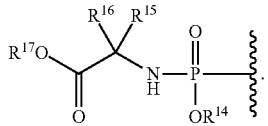

In yet another embodiment, R$^1$ is:

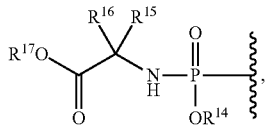

wherein R$^{14}$ is C$_6$-C$_{10}$ aryl, which can be optionally substituted as described above for the Compounds of Formula (I); one of R$^{15}$ and R$^{16}$ is H and the other is C$_1$-C$_6$ alkyl; and R$^{17}$ is C$_1$-C$_6$ alkyl.

In one embodiment, R$^2$ is H.
In one embodiment, R$^3$ is C$_1$-C$_6$ alkyl.
In another embodiment, R$^3$ is methyl.
In one embodiment, R$^3$ is C$_1$-C$_6$ alkyl and R$^{3'}$ is —OH or F.
In another embodiment, R$^3$ is methyl and R$^{3'}$ is —OH or F.
In another embodiment, R$^3$ is methyl and R$^{3'}$ is —OH.
In another embodiment, R$^3$ is methyl and R$^{3'}$ is F.
In one embodiment, R$^6$, R$^{10}$ and R$^{11}$ are each independently —N(R$^{20}$)$_2$ and R$^9$ is —O—CH$_2$—(C$_6$-C$_{10}$ aryl).
In one embodiment, each of R$^1$ and R$^2$ is H.
In one embodiment, R$^1$ is —C(O)—C$_1$-C$_6$ alkyl and R$^2$ is —OC(O)—C$_1$-C$_6$ alkyl.

In another embodiment, $R^1$ is —C(O)-isopropyl and $R^2$ is —OC(O)-isopropyl.

In another embodiment, $R^1$ is —C(O)-isopropyl, $R^2$ is —OC(O)-isopropyl, $R^3$ is methyl and $R^{3'}$ is F.

In one embodiment $R^1$ and and $R^2$ join to form a group having the formula:

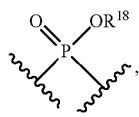

wherein $R^{18}$ is $C_1$-$C_6$ alkyl, $C_3$-$C_7$ cycloalkyl or $C_6$-$C_{10}$ aryl.

In another embodiment, $R^1$ and $R^2$ join to form a group having the formula:

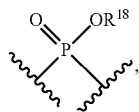

wherein $R^{18}$ is methyl, ethyl, isopropyl, cyclobutyl or phenyl.

In one embodiment, the compounds of formula (I) have the formula (Ia):

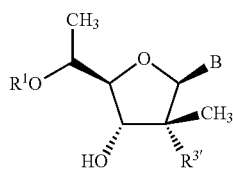

(Ia)

and pharmaceutically acceptable salts thereof, wherein:
B is:

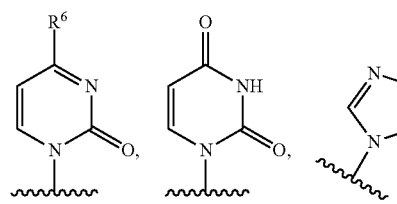

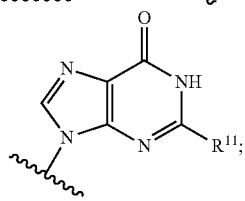

$R^1$ is H or

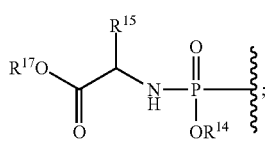

$R^{3'}$ is —OH or halo;
$R^6$, $R^{10}$ and $R^{11}$ are each independently —N($R^{20})_2$;
$R^9$ is —O—CH$_2$—($C_6$-$C_{10}$ aryl);
$R^{14}$ is $C_6$-$C_{10}$ aryl;

$R^{15}$ is $C_1$-$C_6$ alkyl; and
$R^{17}$ is $C_1$-$C_6$ alkyl; and
each occurrence of $R^{20}$ is independently H, —C(O)—($C_1$-$C_6$ alkyl) or —C(O)—($C_6$-$C_{10}$ aryl).

In one embodiment, for the compounds of formula (I) or (Ia), B is:

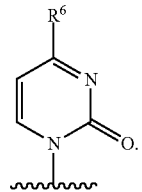

In another embodiment, for the compounds of formula (I) or (Ia), B is:

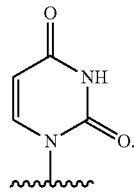 [SMILES: *n1ccc(=O)[nH]c1=O]

In another embodiment, for the compounds of formula (I) or (Ia), B is:

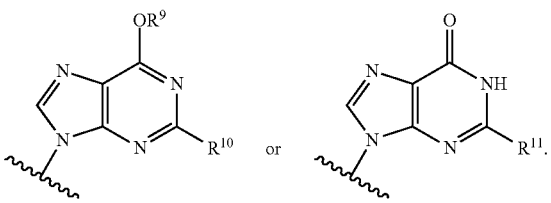

In one embodiment, for the compounds of formula (I) or (Ia), B is:

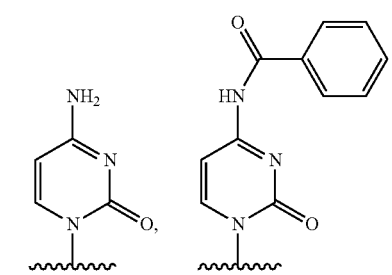

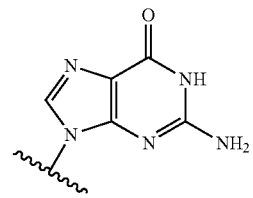

or

-continued

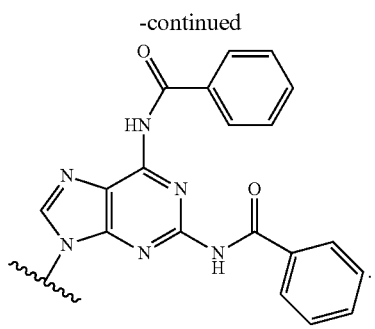

In another embodiment, for the compounds of formula (I) or (Ia), B is:

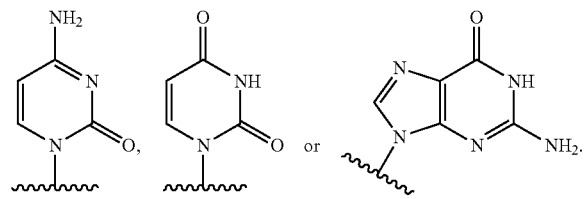

In another embodiment, for the compounds of formula (I) or (Ia), B is:

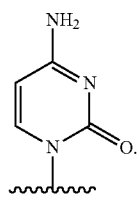 [SMILES: *n1ccc(N)nc1=O]

In still another embodiment, for the compounds of formula (I) or (Ia), B is:

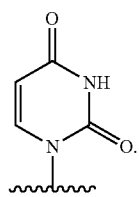 [SMILES: *n1ccc(=O)[nH]c1=O]

In another embodiment, for the compounds of formula (I) or (Ia), B is:

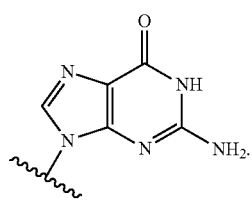 [SMILES: *n1cnc2c(=O)[nH]c(N)nc21]

In another embodiment, for the compounds of formula (I) or (Ia), B is:

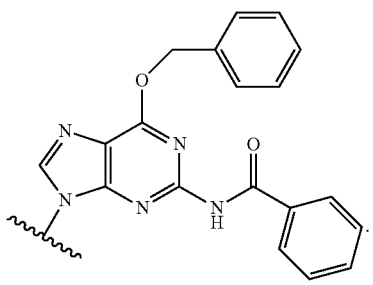 [SMILES: *n1cnc2c(OCc3ccccc3)nc(NC(=O)c3ccccc3)nc21]

In one embodiment, for the compounds of formula (I) or (Ia), $R^1$ is H or

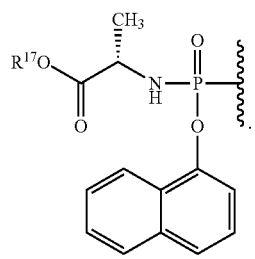

In another embodiment, for the compounds of formula (I) or dal. $R^1$ is:

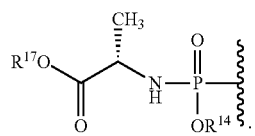

In another embodiment, for the compounds of formula (I) or (Ia), $R^1$ is:

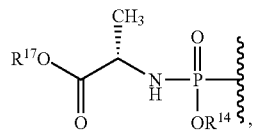

wherein $R^{14}$ is $C_6$-$C_{10}$ aryl, which can be optionally substituted as described above for the Compounds of Formula (I); and $R^{17}$ is $C_1$-$C_6$ alkyl.

In a further embodiment, for the compounds of formula (I) or (Ia), $R^1$ is:

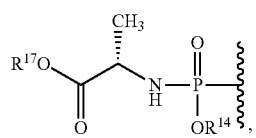

wherein $R^{14}$ is naphthyl or phenyl, which can be optionally substituted with F or Cl; and $R^{17}$ is methyl, ethyl, isopropyl, n-butyl or neopentyl.

In another embodiment, for the compounds of formula (I) or (Ia), R¹ is:
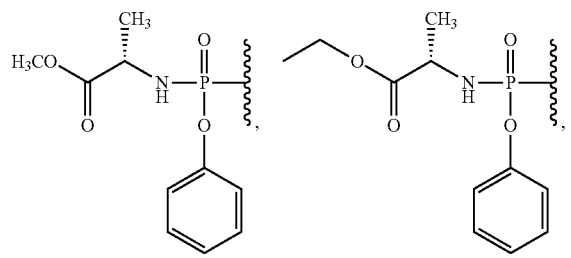
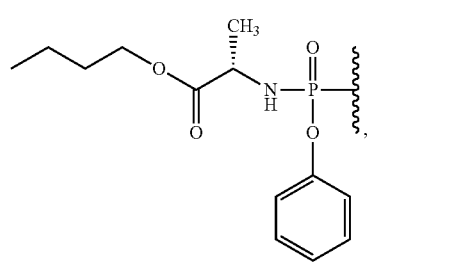
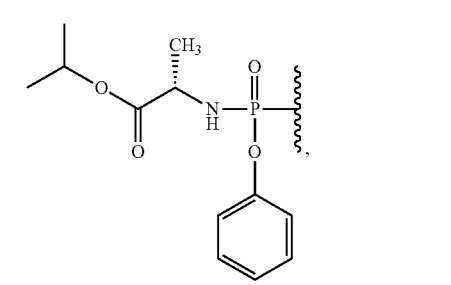
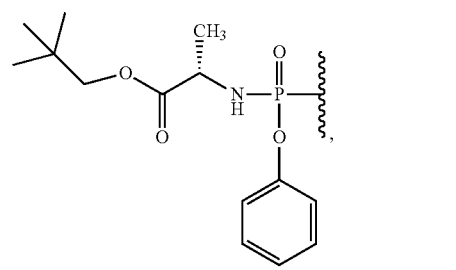
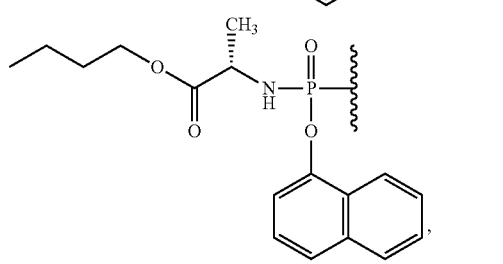
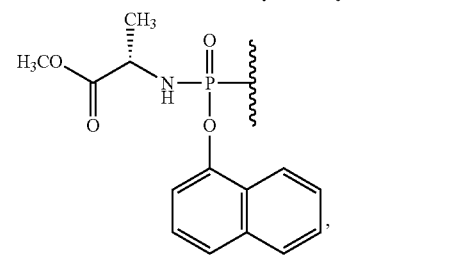
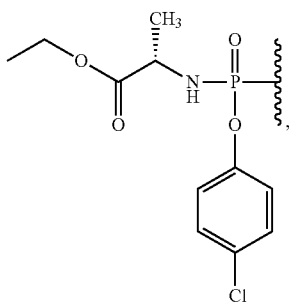
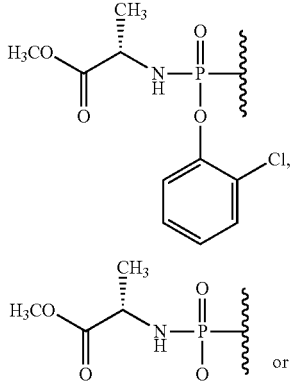
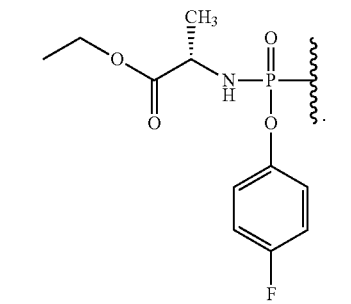
In another embodiment, for the compounds of formula (I) or (Ia), R¹ is
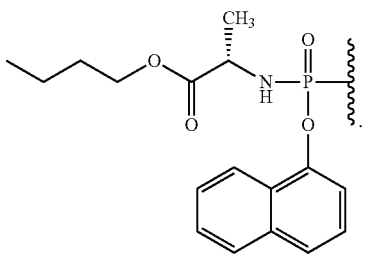 [SMILES: *P(=O)(N[C@@H](C)C(=O)OCCCC)Oc1cccc2ccccc12]
In another embodiment, for the compounds of formula (I) or (Ia), R¹ is H.

In another embodiment, for the compounds of formula (I) or (Ia), $R^1$ is

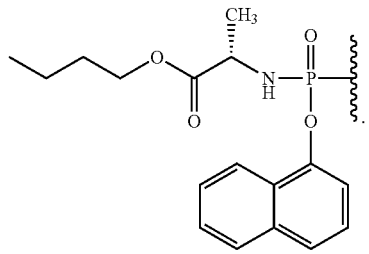 [SMILES: *P(=O)(N[C@@H](C)C(=O)OCCCC)Oc1cccc2ccccc12]

In one embodiment, for the compounds of formula (I) or (Ia), $R^{3'}$ is —OH or F.

In another embodiment, for the compounds of formula (I) or (Ia), $R^{3'}$ is —OH.

In another embodiment, for the compounds of formula (I) or (Ia), $R^{3'}$ is F.

In one embodiment, for the compounds of formula (I) or (Ia), B is:

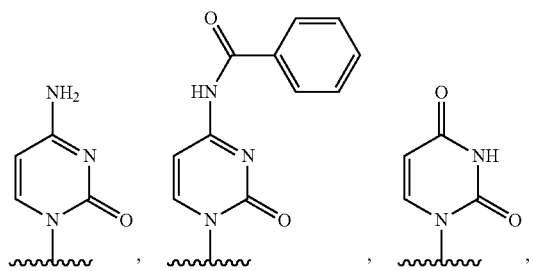

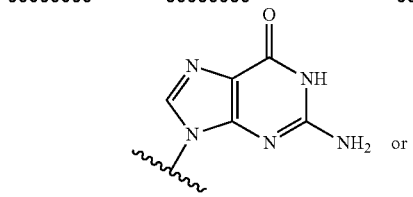

or

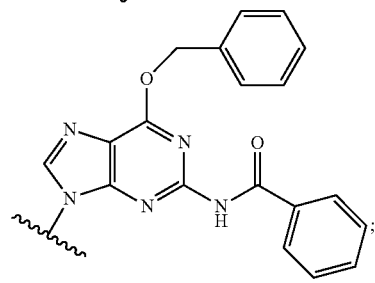

$R^1$ is H or

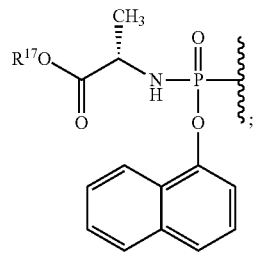

and
$R^{3'}$ is —OH or F.

In another embodiment, for the compounds of formula (I) or (Ia), B is:

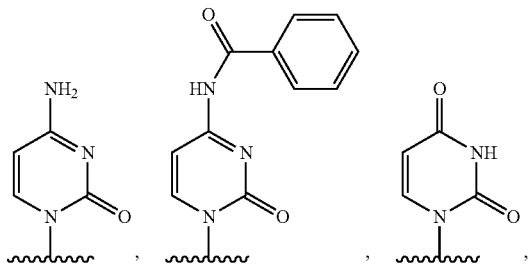

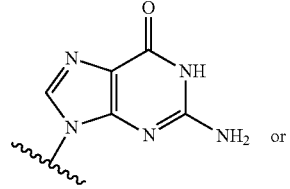

or

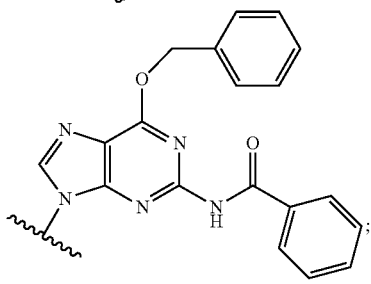

$R^1$ is

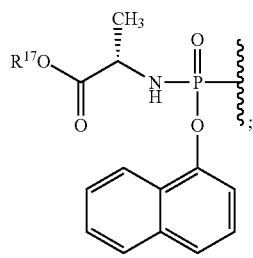

and
$R^{3'}$ is —OH.

In another embodiment, for the compounds of formula (I) or (Ia), B is:

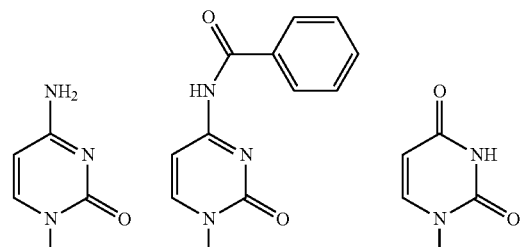

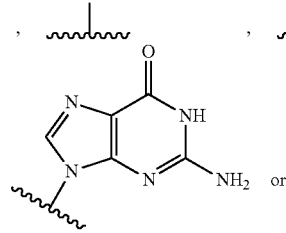

or

-continued

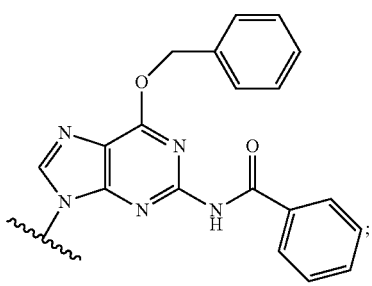

R[1] is

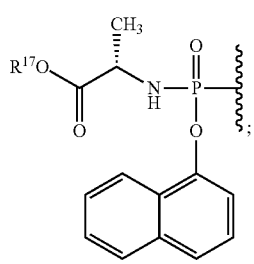

and

R[3'] is F.

In still another embodiment, for the compounds of formula (I) or (Ia), B is:

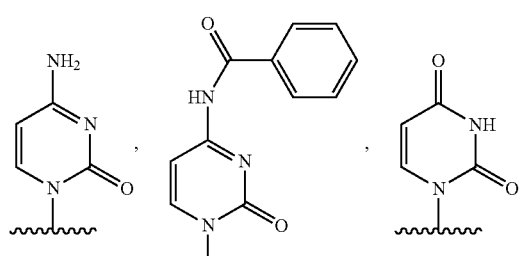

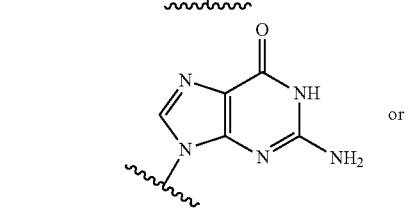

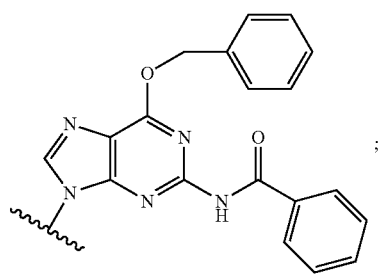

R[1] is H; and
R[3'] is —OH.

In another embodiment, for the compounds of formula (I) or (Ia), B is:

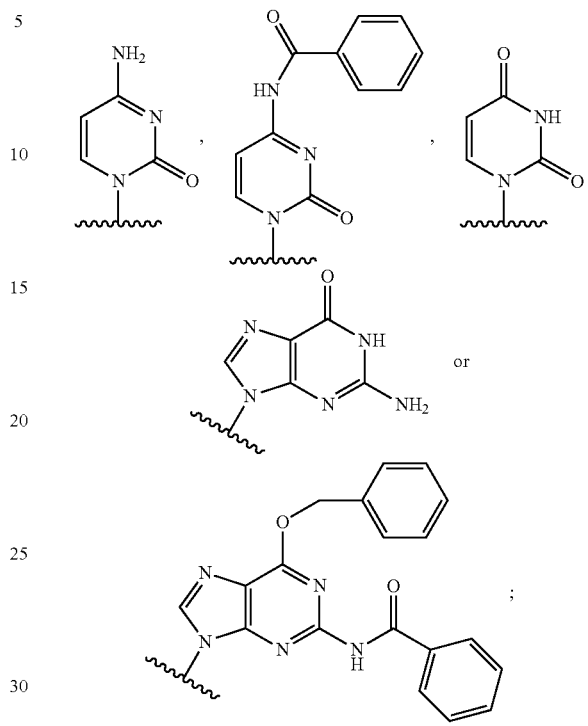

R[1] is H; and
R[3'] is F.

In one embodiment, variables B, X, Z, R[1], R[2], R[3] and R[3'] for the Compounds of Formula (I) are selected independently of each other.

In one embodiment, variables B, R' and R[3'] for the Compounds of Formula (Ia) are selected independently of each other.

In another embodiment, the Compounds of Formula (I) or (Ia) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-30 as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-E below. Alternative synthetic pathways and analogous structures will be apparent to those skilled in the art of organic synthesis.

Scheme A shows a method useful for making nucleoside compounds of formula A11, which correspond to the Compounds of Formula (I), wherein X is O; $R^1$ and $R^2$ are each H; $R^3$ is methyl; $R^{3'}$ is —OH; and B and Z are defined above for the Compounds of Formula (I).

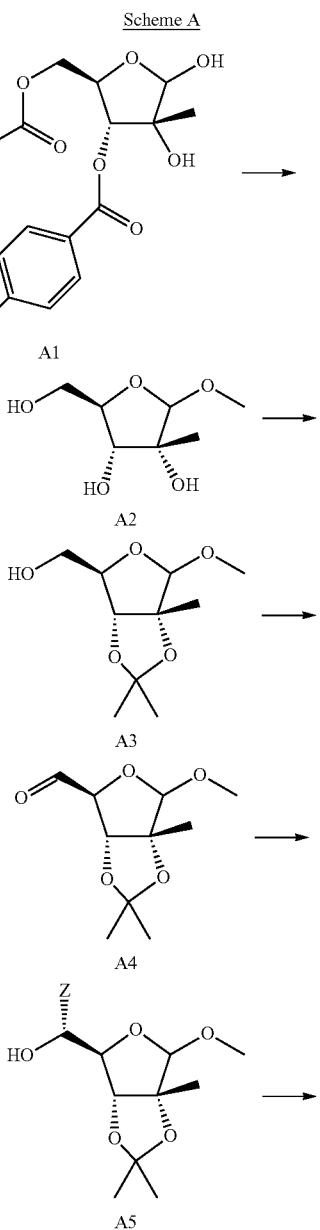

Scheme A

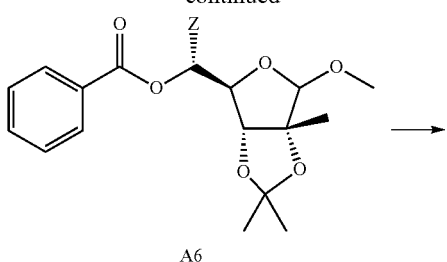

A6

Scheme A

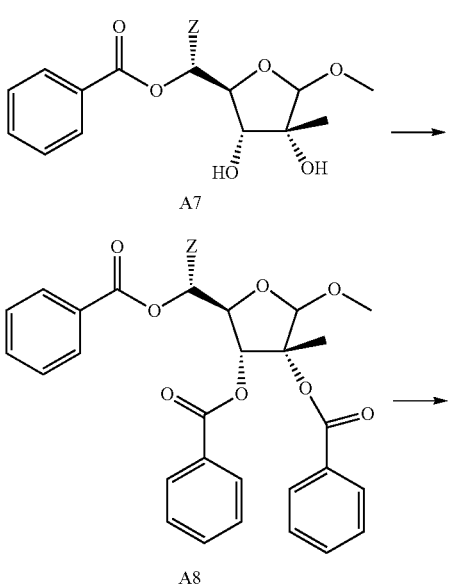

A7

A8

A9

A10

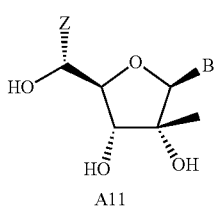

A11

Ribose compounds of formula A1 can be protected at the 1' position using methanol, followed by in-situ hydrolysis of the benzoates to provide compounds of formula A2. Compounds of formula A2 can be protected as the 2'-3' acetonide using 2,2-dimethxypropane, to provide a compounds of formula A3. Oxidation of the 5'-OH group with reagents such as 2,2,6,6,-tetramethylpiperidinyloxy (TEMPO) and diacetoxyiodobenzene for example, provides compounds of formula A4, the aldehyde moiety of which, can be treated with an appropriate alkyl nucleophile, such as methyl Grignard, to provide compounds of formula A5. The resulting hydroxyl group can be protected as the benzoate using, for example, benzoyl chloride, to provide the compounds of formula A6. The acetonide of A6 can then be removed in the presence of acid (such as trifluoroacetic acid) to provide the compounds of formula A7. The resulting diol of A7 can be reprotected with benzoates using benzoyl chloride to provide compounds of formula A8. and the 1' position of A8 can then be converted to an acetate with the use of sulfuric acid, acetic acid, and acetic anhydride to provide compounds of formula A9. Glycosylation with the appropriately protected base provides compounds of formula A10, which can then be globally deprotected using ammonia/ammonium hydroxide to provide the nucleosides of formula A11.

Scheme B shows an alternate method useful for making nucleoside compounds of formula B3, which correspond to the Compounds of Formula (I), wherein X is O; $R^1$ and $R^2$ are each H; $R^3$ is methyl; $R^{3'}$ is —OH; and B and Z are defined above for the Compounds of Formula (I).

Scheme B

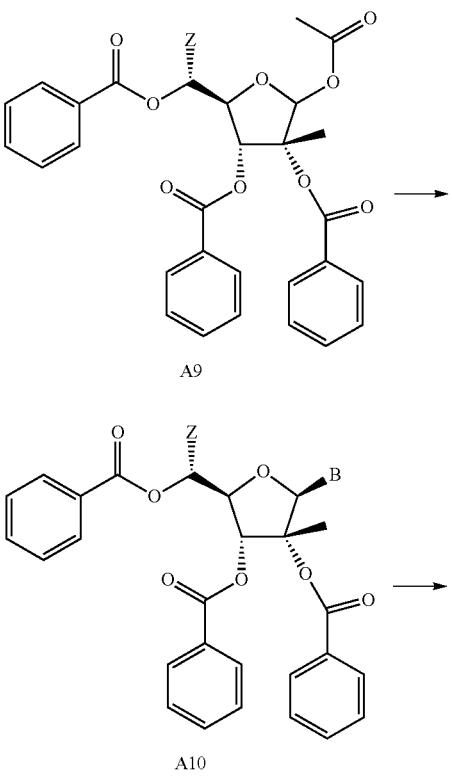

A5

B1

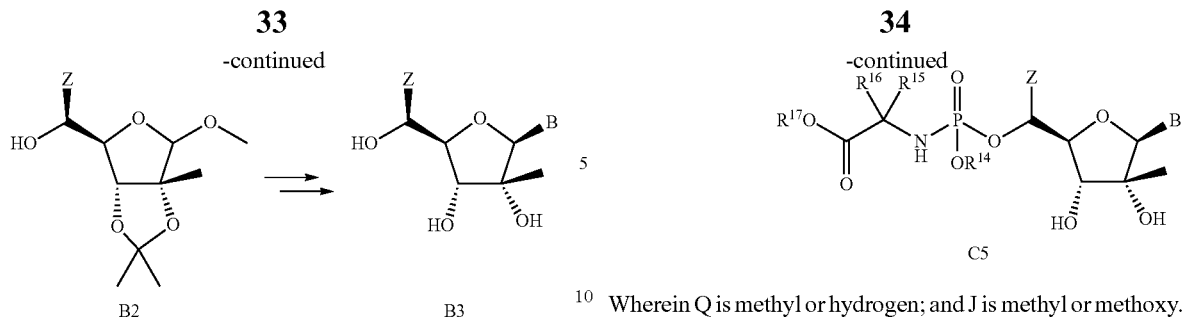

B2 → B3

Compounds of formula A5 can be inverted at the 5' position using 4-NO$_2$-benzoic acid to provide compounds of formula B1. Compounds of formula B2 can be prepared via hydrolysis of the benzoate moiety of B1 using sodium hydroxide. Compounds of formula B2 can then be converted to compounds of formula B3 using the methods described above in Scheme A.

Scheme C shows a method useful for making nucleoside compounds of formula C5, which correspond to the Compounds of Formula (I), wherein X is O; R' is:

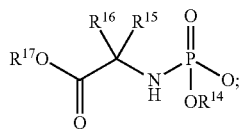

R$^2$ is H; R$^3$ is methyl; R$^{3'}$ is —OH; and B, Z, R$^{14}$, R$^{15}$, R$^{16}$, and R$^{17}$ are defined above for the Compounds of Formula (I).

Wherein Q is methyl or hydrogen; and J is methyl or methoxy.

A compound of formula C1 can have its 2' and 3' hydroxyl groups protected using well known methods to provide the compounds of formula C2. A compound of formula C2 can then be coupled with a compound of formula C3 (compounds of formula C3 can be made using methods described in U.S. Pat. No. 7,879,815) in the presence of either tert-butylmagnesium bromide or N-methylimidazole to provide the compounds of formula C4, the diol of which can be deprotected using formic acid and hydrochloric acid to provide compounds of formula C5.

Scheme D shows a method useful for making nucleoside compounds of formula D8, which correspond to the Compounds of Formula (I), wherein X is O; R$^1$ and R$^2$ are each H; R$^3$ is methyl; R$^{3'}$ is F; B is:

and Z is defined above for the Compounds of Formula (I).

Scheme C

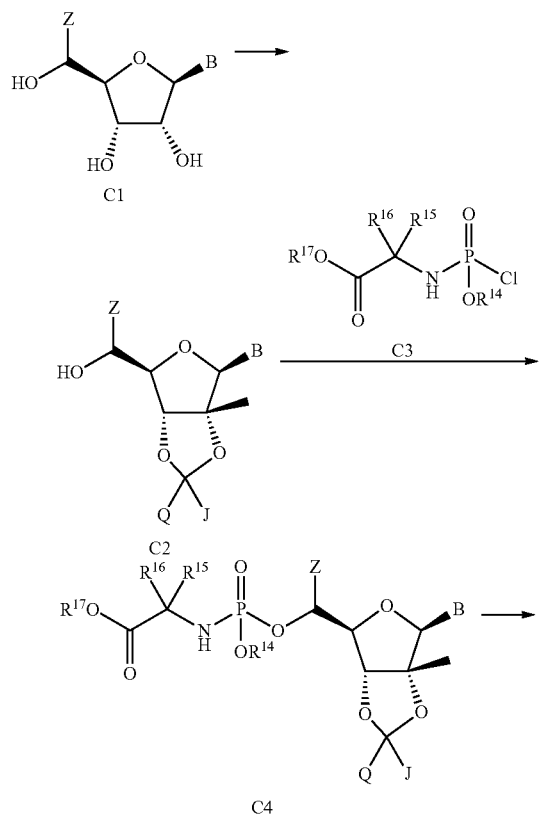

Scheme D

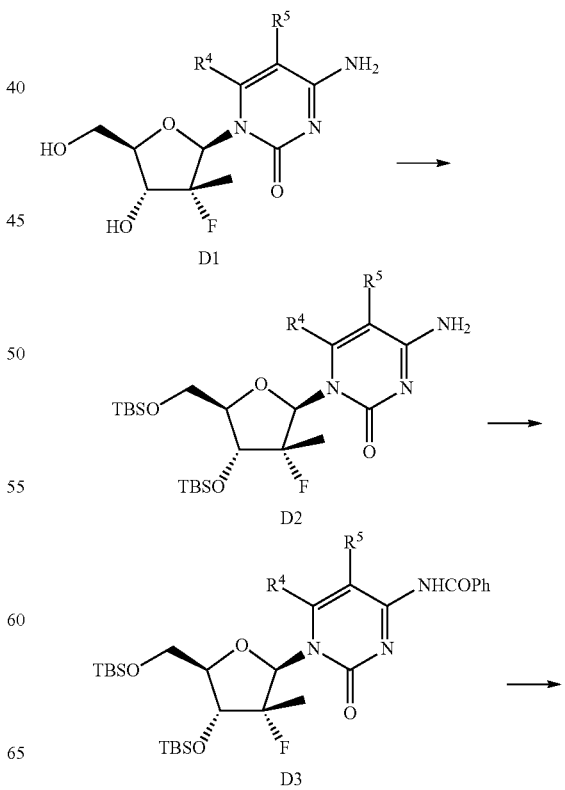

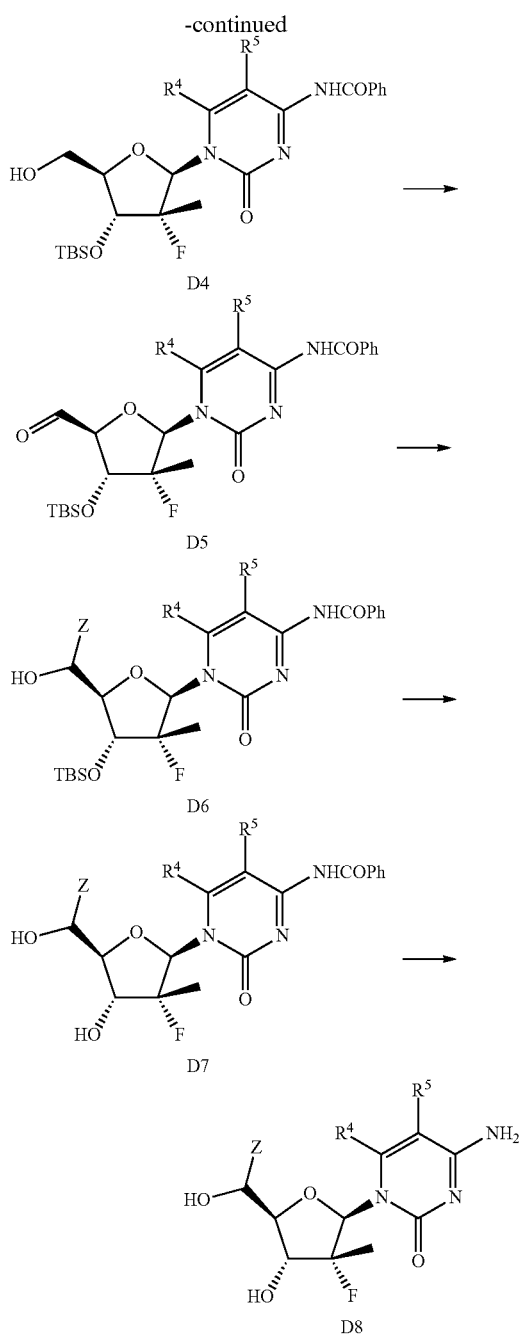

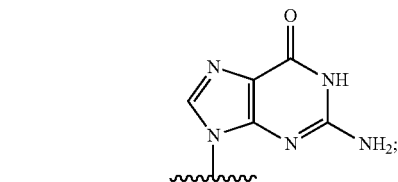 [SMILES: *n1cnc2c(=O)[nH]c(N)nc21]

nium fluoride to provide compounds of formula D7. Further deprotection of compounds of the formula D7 utilizing ammonia in methanol provides compounds of formula D8.

Scheme E shows a method useful for making nucleoside compounds of formula E9, which correspond to the Compounds of Formula (I), wherein X is O; $R^1$ and $R^2$ are each H; $R^3$ is methyl; $R^3$ is F; B is:

and Z is defined above for the Compounds of Formula (I).

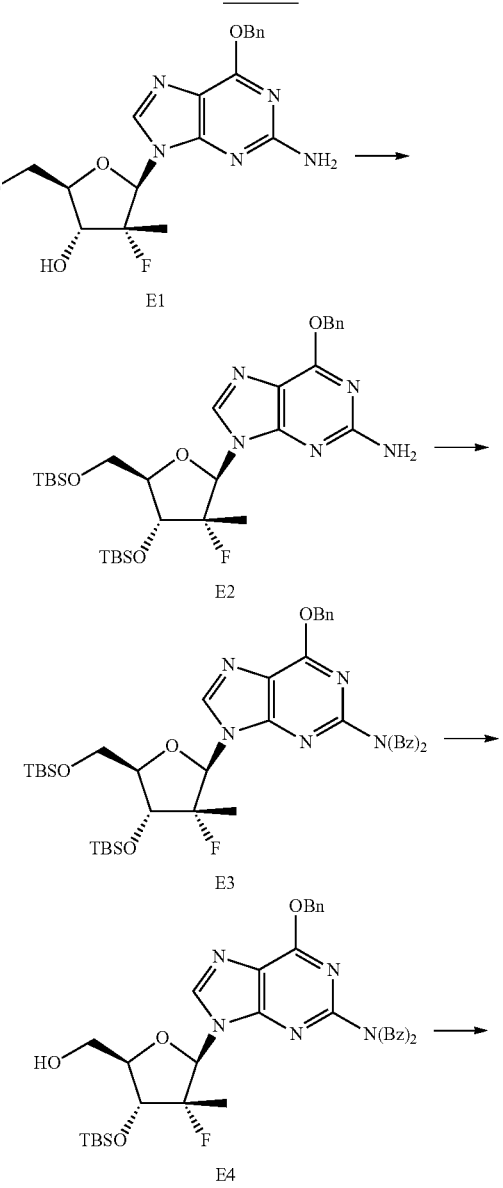

Compounds of formula D1 (which can be made using methods described in US Patent Publication No. US 2010/0056770) can be protected at the hydroxyl groups using tertbutyldimethylsilyl chloride and imidazole, for example to provide compounds of formula D2. Compounds of formula D2 can be further protected using benzoyl chloride and pyridine to provide compounds of formula D3. Compounds of formula D3 can be selectively deprotected at the 5' hydroxyl using trifluoroacetic acid to provide compounds of formula D4. Oxidation using, for example, Dess-Martin periodinane, can furnish compounds of formula D5. The aldehyde moiety of the compounds of formula D5 can be treated with the appropriate nucleophile, such as methyl Grignard, to provide compounds of formula D6. Deprotection of the remaining hydroxyl group can be accomplished with tetrabutylammo-

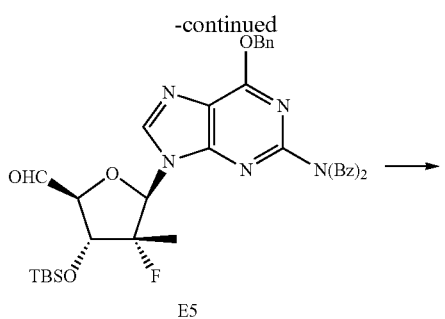

E5

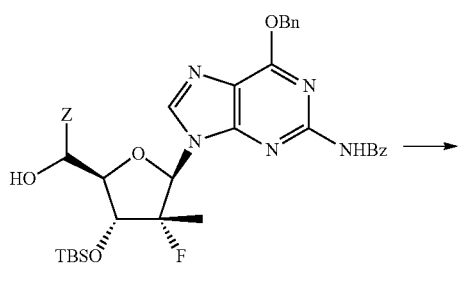

E6

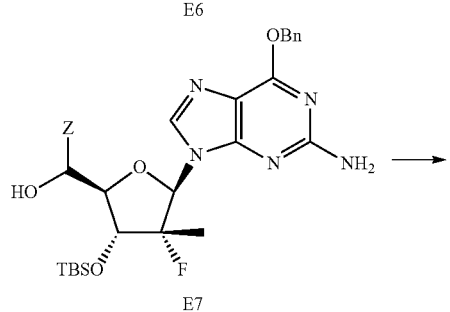

E7

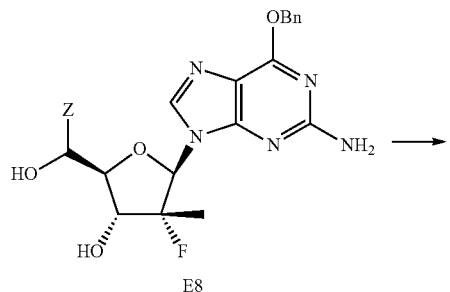

E8

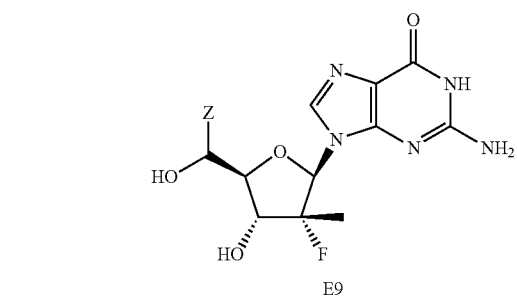

E9

Compounds of formula E1 (which can be made using methods described in International Publication No. WO 2010/075549) can have their free hydroxyl groups globally protected as their TBDMS ethers to provide compounds of formula E2. The amino group E2 can then be protected using benzoyl chloride and pyridine to provide compounds of formula E3. Compounds of formula E3 can be selectively deprotected at the 5'-hydroxyl using trifluoroacetic acid to provide compounds of formula E4, the free hydroxy group of which can be oxidized using, for example, the Dess-Martin periodinane, to provide aldehyde compounds of formula E5, The compounds of formula E5 can then be treated with an appropriate nucleophile, such as methyl Grignard, to provide compounds of formula E6. Deprotection of the N-benzoyl group in the purine base of compounds of the formula E6 utilizing ammonia in methanol provides compounds of formula E7. Further deprotection of the 3'-hydroxyl group of E7 can then be accomplished with tetrabutylammonium fluoride to provide compounds of formula E8. Finally, deprotection of the purine benzyl ether moiety of E8 using hydrogen gas and palladium provides the compounds of formula E9.

Compounds of formula A11, B3, C5, D8 and E9 can be further elaborated using methods that would be well-known to those skilled in the art of organic synthesis or, for example, the methods described in the Examples below, to make the full scope of the Compounds of Formula (I).

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Schemes A-E may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from $Me_4Si$ with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% $CH_3CN$, 5 minutes—95% $CH_3CN$, 5-7 minutes—95% $CH_3CN$, 7 minutes—stop. The parent ion is given. Flash chromatography on silica gel was performed using pre-packed normal phase silica from Isco, Biotage, Inc. or bulk silica from Fisher Scientific. Unless otherwise indicated, flash chromatography on silica

Example 1
Preparation of Compound 1
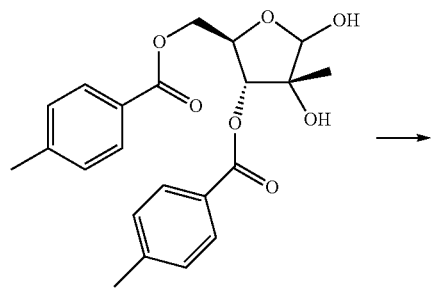
1a
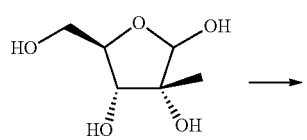
1b
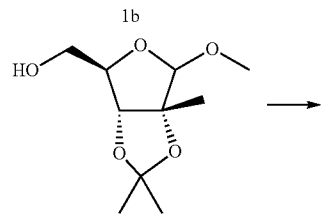
1c
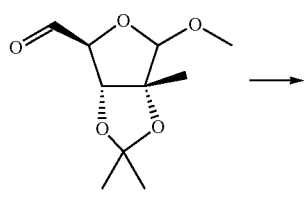
1d
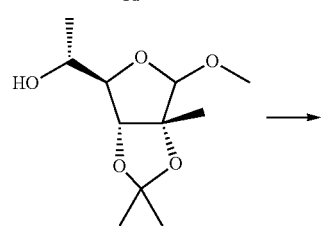
1e
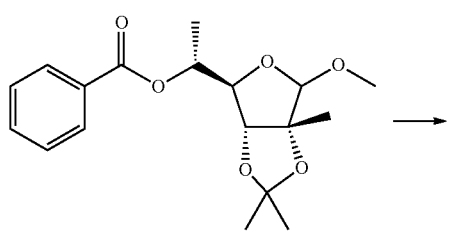
1f
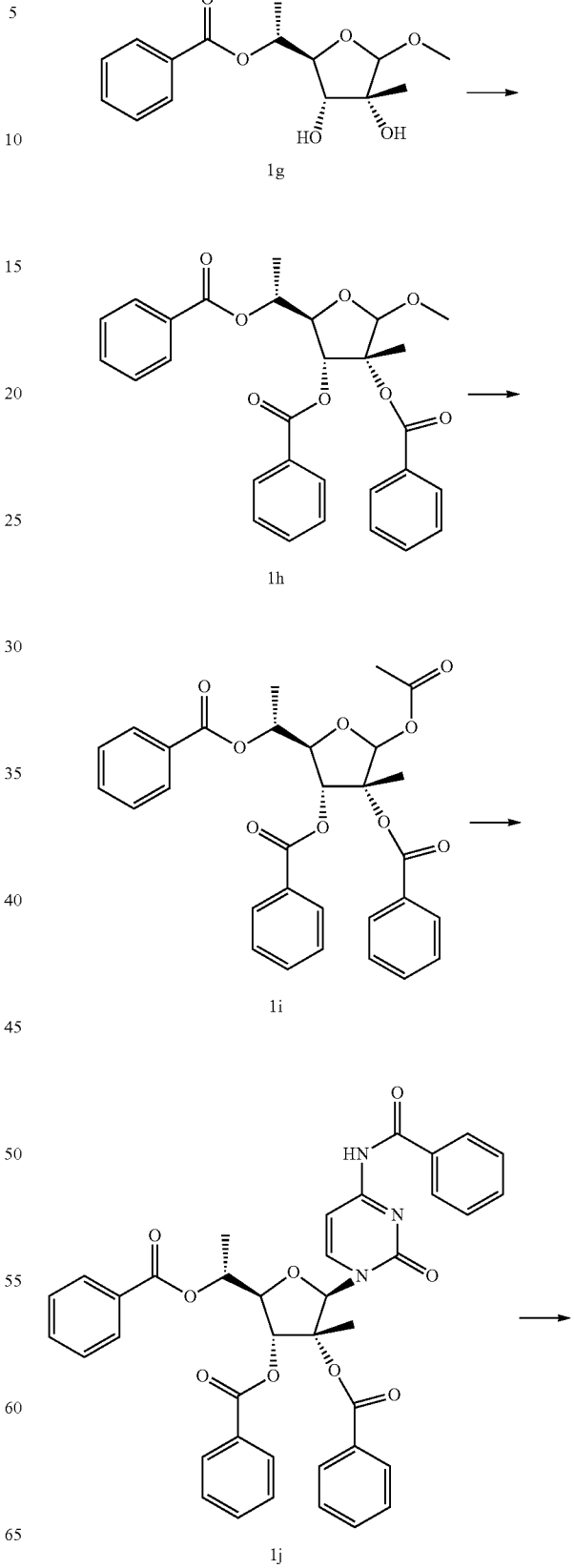

-continued

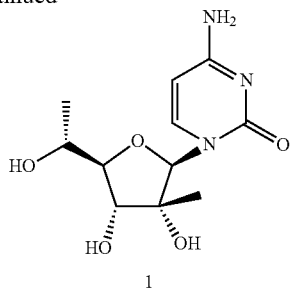

1

Step A—Synthesis of Compound 1b

TsOH—H$_2$O (1.5 g) was added to a solution of compound 1a (30 g, made according to the method described in *J. Org. Chem.*, 2004, 69, 6257-6266) in methanol (200 mL) and the resulting reaction was allowed to stir at 50° C. for about 15 hours. The reaction was cooled to room temperature and NaOH (9.3 g) was added and the resulting reaction was allowed to stir for 2 hours, then the reaction mixture was concentrated in vacuo to provide the crude material 1b, which was used without further purification.

Step B—Synthesis of Compound 1c

To compound 1b was added acetone (150 mL) and then 2,2-dimethyoxypropane (150 mL). To the resulting solution methanesulfonic acid (10 mL) was added, and the reaction mixture was allowed to stir for 4 hours at room temperature. Acetone (80 mL) was added and the reaction was allowed to stir for an additional 22 hours. Additional acetone (100 mL) and DMP (30 mL) were added, followed by methanesulfonic acid (10 mL) until all material dissolved and the resulting reaction was allowed to stir for an additional 25 hours. The reaction was diluted with EtOAc and filtered and the filtrate was diluted with water and extracted with EtOAc (2×100 mL). The combined organic extracts were separated, dried over sodium sulfate, filtered and concentrated in vacuo. The resulting residue was purified using flash column chromatography on silica gel on silica gel using 0 to 50% EtOAc/hexane to provide compound 1e (14.5 g).

Step C—Synthesis of Compound 1d

Compound 1c (14.5 g, 65 mmol) was taken up in dichloromethane (400 mL) and to the resulting solution was added TEMPO (1 g, 6.4 mmol), followed by diacetoxyiodobenzene (23.5 g, 71.5 mmol) was then added and the resulting reaction was allowed to stir at room temperature for about 15 hours. The reaction was quenched with saturated aqueous NaHCO$_3$ and allowed to stir vigorously for 1 hour. The reaction mixture was then extracted with EtOAc (3×~400 mL) and the combined organic extracts were dried over sodium sulfate, filtered and concentrated in vacuo. The resulting residue was purified using flash column chromatography on silica gel using 0 to 50% EtOAc/hexane to provide compound 1d (9 g).

Step D—Synthesis of Compound 1e

A solution of compound 1d (9 g, 42 mmol) in THF (215 mL). was cooled to −78° C. and to the cooled solution was added MeMgBr (47 mL, 3M in ether, 141 mmol) via an addition funnel. The reaction was allowed to warm up to 10° C. over 6 hours with stirring, then was quenched with saturated aqueous NH$_4$Cl and diluted with H$_2$O and extracted with EtOAc. The organic extract was dried over sodium sulfate, filtered and concentrated in vacuo. The resulting residue was purified using flash column chromatography on silica gel using 0 to 40% EtOAc/hexane to provide compound 1e (8.1 g, 83%).

Step E—Synthesis of Compound 1f

To a solution of compound 1e (5 g, 8.6 mmol) in dichloromethane (40 mL) was added pyridine (4 mL), benzoyl chloride (5 mL) and DMAP (1.2 g). The resulting reaction was allowed to stir at room temperature for about 15 hours, then was quenched with NaHCO$_3$, extracted with EtOAc (2×40 mL) and then washed with 1N HCl. The combined organic extracts were dried over sodium sulfate, filtered and concentrated in vacuo. The resulting residue was purified using flash column chromatography on silica gel using 0 to 30% EtOAc/hexane to provide compound 1f (5.4 g).

Step F—Synthesis of Compound 1g

To compound 1f (5.4 g) was added aqueous TFA (18 mL in 2 mL water) and the resulting reaction was allowed to stir for 1 hour. The reaction was quenched with saturated aqueous NaHCO$_3$ and extracted with EtOAc (3×15 mL). The combined organic extracts were dried over MgSO$_4$, filtered and concentrated in vacuo to provide compound 1g, which was used without further purification.

Step G—Synthesis of Compound 1h

To a solution of benzoyl chloride (5.5 mL) in acetonitrile (10 mL) was added triethylamine (9 mL). The resulting solution turned yellow-orange, then a solution of compound 1g in acetonitrile (20 mL) was added, followed by DMAP (1 g). The resulting reaction was allowed to stir for about 60 hours, then saturated aqueous NaHCO$_3$ was added slowly until gas evolution ceased and the mixture was extracted with EtOAc (2×20 mL). The combined organic extracts were washed with 1N HCl, dried over MgSO$_4$, filtered and concentrated in vacuo. The resulting residue was purified using flash column chromatography on silica gel using 0 to 30% EtOAc/hexane to provide compound 1h (6.4 g, 79%).

Step H—Synthesis of Compound 1i

To a 0° C. solution of compound 1h (6.4 g) in dichloromethane (24 mL) was added acetic anhydride (5.8 mL), acetic acid (4.7 mL) and H$_2$SO$_4$ (1 mL) and the resulting solution was cooled to 0° C. This cooled solution was then added to a solution of compound 1h in dichloromethane and the resulting reaction was allowed to stir for 2 hours, then was quenched with saturated aqueous NaHCO$_3$. The reaction mixture was extracted with EtOAc (3×~20 mL) and the combined organic extracts were dried over MgSO4, filtered and concentrated in vacuo. The resulting residue was purified using flash column chromatography on silica gel using 0 to 30% EtOAc/hexane to provide compound 1i (4.5 g, 67%).

Step I—Synthesis of Compound 1j

Compound 1i (30 mg, 0.056 mmol) was taken up in acetonitrile (2 mL) and to the resulting solution was added N-(2-oxo-1,2-dihydropyrimidin-4-yl)benzamide (36 mg, 0.169 mmol), followed by bis(trimethylsilyl)acetamide (82 μL, 0.336 mmol). The resulting reaction was heated to 90° C. and allowed to stir at this temperature for 30 minutes. The reaction was then cooled to 0° C. and TMSOTf (35 μL, 0.194 mmol) was added dropwise. The resulting reaction was allowed to warm to room temperature on its own, then the reaction mixture was heated to 90° C. and allowed to stir at this temperature for 3 hours. The reaction was then cooled to room temperature, quenched with saturated aqueous NaHCO$_3$ and extracted with chloroform (2×5 mL). The combined organic extracts were dried over sodium sulfate, filtered and concentrated in vacuo. The resulting residue was purified using flash column chromatography on silica gel using 0-60% EtOAc/hexane to provide compound 1j (24 mg).

Step J—Synthesis of Compound 1

A solution of compound 1j in 7N NH$_3$ in methanol (5 mL) was heated to 90° C. and allowed to stir at this temperature for about 15 hours. The reaction mixture was then cooled to room temperature and concentrated in vacuo. The resulting residue was purified using flash column chromatography on silica gel using 0 to 20% methanol/EtOAc+1% NH₄OH to provide compound 1 (30 mg). LC/MS=272.2

Example 2

Preparation of Compound 2

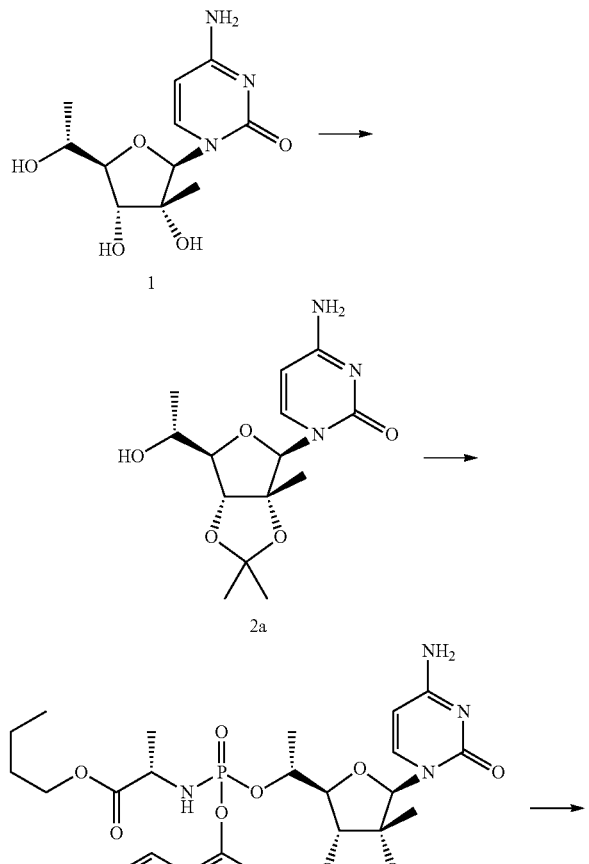

Step A—Synthesis of Compound 2a

Compound 1 (28 mg) was taken up in acetone (2.5 mL) and to the resulting suspension was added DMP (150 µL), fol lowed by TsOH—H₂O (25 mg). The resulting reaction was allowed to stir at room temperature for about 15 hours and was then heated to 60° C. for 5 hours. The reaction mixture was concentrated in vacuo and the resulting residue was taken up in methanol (5 ml). Basic resin Amberlyst A26b (catalytic) was added and the resulting solution was allowed to stir at room temperature for 1 hour. The reaction mixture was filtered and concentrated in vacuo to provide compound 2a (31 mg), which was pure by NMR and used as is.

Step B—Synthesis of Compound 2b

To a 0° C. solution of compound 2a (31 mg) in THF (3 mL) was added t-BuMgCl (300 µL) the resulting solution was allowed sto stir at room temperature for 15 minutes. Phosphorochloridate (111 mg) was then added and the resulting reaction was allowed to stir at room temperature for about 15 hours. The reaction was cooled to 0° C. and t-BuMgCl (600 µL) was added and the resulting solution was allowed to stir for 10 minutes, then additional phosphochloridate (222 mg) was added and let stir for about 16 hrs at room temperature. The reaction was then diluted with EtOAc and was washed with H₂O and brine, dried over MgSO₄, filtered and concentrated in vacuo. The resulting residue was purified using flash column chromatography on silica gel using 0 to 20% methanol/dichloromethane to provide compound 2b (3 mg).

Step C—Synthesis Of Compound 2

Aqueous formic acid (5 mL, 80%) was added to compound 2b (3 mg) followed by 100 µL HCl (4M in dioxane) and the resulting reaction was allowed to stir at room temperature for about 15 hours. The reaction mixture was concentrated in vacuo and the residue obtained was purified using flash column chromatography on silica gel using 0 to 20% methanol/dichloromethane to provide compound 2 (1.4 mg). LC/MS=605.2.

Example 3

Preparation of Compound 3

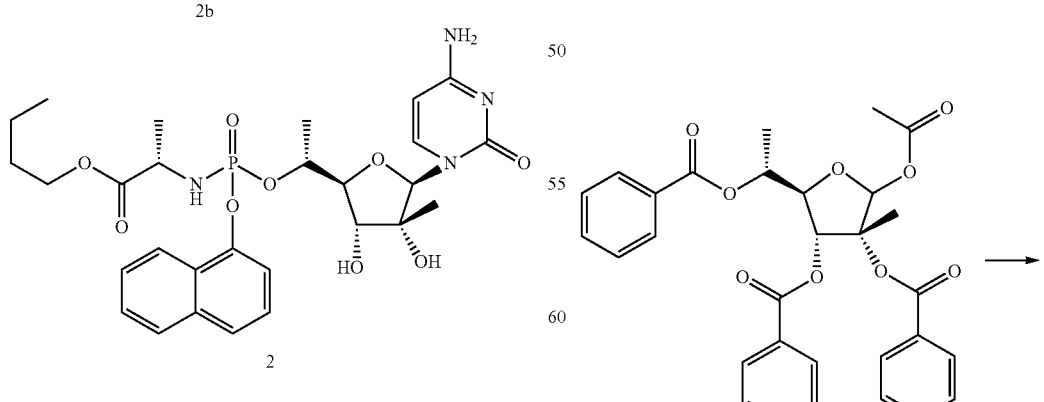

1i

Example 4

Preparation of Compound 4

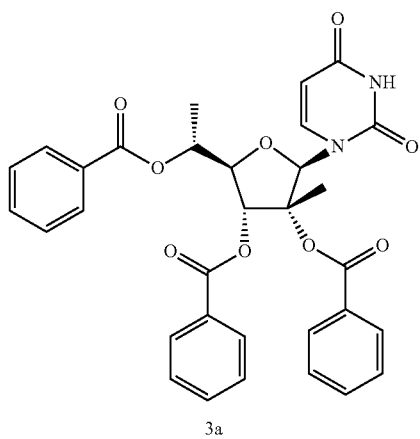

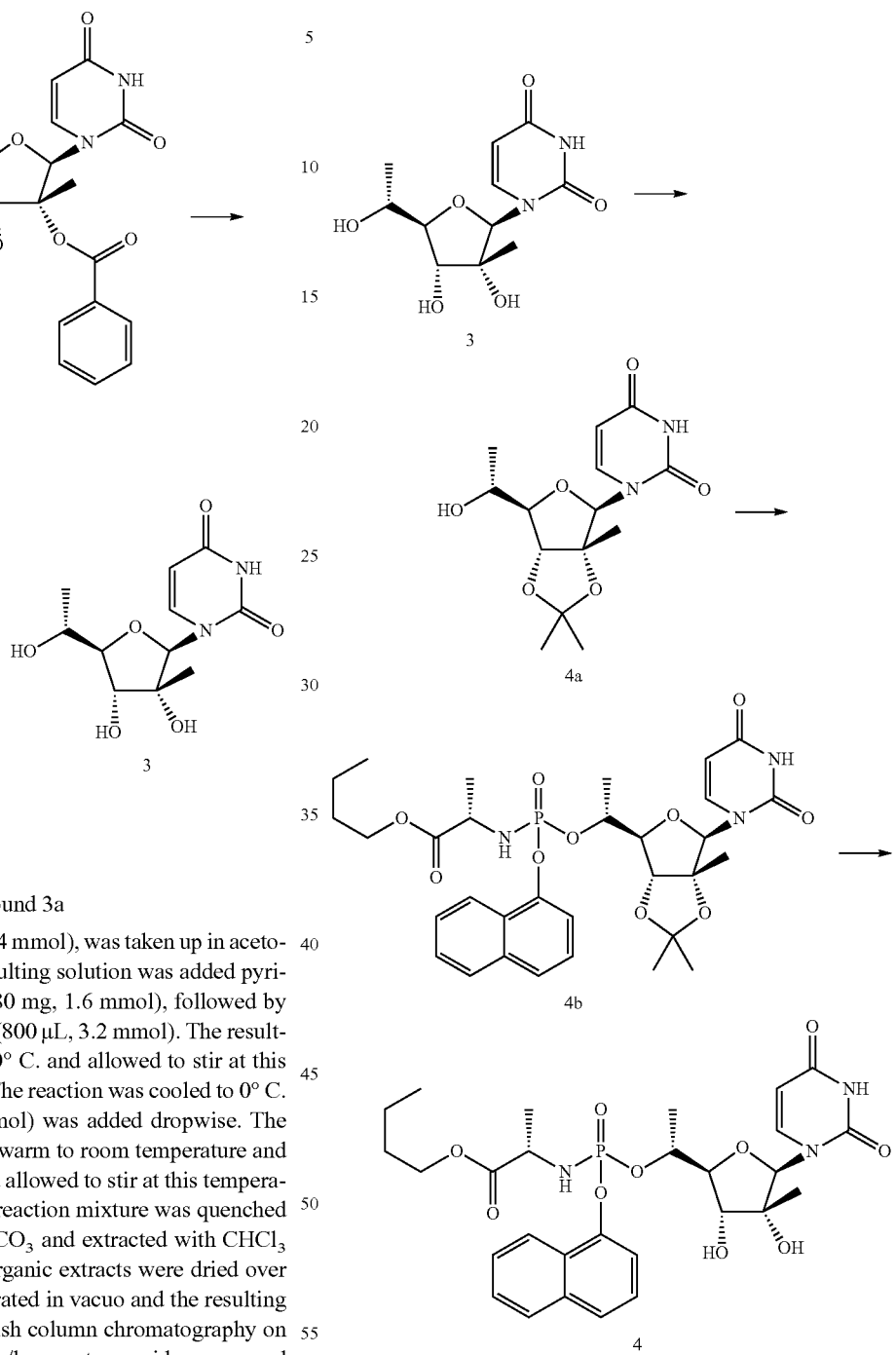

Step A—Synthesis of Compound 3a

Compound 1i (300 mg, 0.54 mmol), was taken up in acetonitrile (20 mL) and to the resulting solution was added pyrimidine-2,4(1H,3H)-dione (180 mg, 1.6 mmol), followed by bis(trimethylsilyl)acetamide (800 µL, 3.2 mmol). The resulting reaction was heated to 90° C. and allowed to stir at this temperature for 30 minutes. The reaction was cooled to 0° C. and TMSOTf (350 µL, 2 mmol) was added dropwise. The reaction was then allowed to warm to room temperature and then was heated to 90° C. and allowed to stir at this temperature for about 15 hours. The reaction mixture was quenched with saturated aqueous NaHCO$_3$ and extracted with CHCl$_3$ (3×20 mL). The combined organic extracts were dried over MgSO$_4$, filtered and concentrated in vacuo and the resulting residue was purified using flash column chromatography on silica gel using 0-60% EtOAc/hexane to provide compound 3a (100 mg).

Step B—Synthesis of Compound 3

A solution of compound 3a in 7N NH3 in methanol (5 mL) and NH$_4$OH (1 mL) and heated to 90° C. and allowed to stir at this temperature for about 15 hours. The reaction was cooled to room temperature, concentrated in vacuo, and the resulting residue was purified using flash column chromatography on silica gel using 0 to 20% methanol/EtOAc to provide compound 3 (38 mg). LC/MS=295.2 (M+Na)$^+$

Step A—Synthesis of Compound 4a

Compound 3 (38 mg) was taken up in acetone (3.5 mL) and to the resulting suspension was added DMP (200 µL), followed by TsOH—H$_2$O (33 mg). The resulting reaction was allowed to stir at room temperature for about 60 hours, then was quenched with NaHCO$_3$. The reaction mixture was then extracted with EtOAc (3×~5 mL) and the combined organic extracts were dried over MgSO$_4$, filtered and concentrated in vacuo to provide compound 4a (30 mg), which was used without further purification.

Step B—Synthesis of Compound 4b

Compound 4a (30 mg) was taken up in THF (1.5 mL) and to the resulting solution was added phosphorochloridate (185 mg). The resulting reaction was cooled to −78° C., N-methyl imidazole (50 µL) was added, the cold bath was removed, and the resulting reaction was allowed to stir at room temperature for about 15 hours. The reaction was quenched with EtOAc and was washed with H₂O and brine, dried over MgSO₄, filtered and concentrated in vacuo. The resulting residue was purified using flash column chromatography on silica gel using 0 to 20% methanol/dichloromethane to provide compound 4b (30 mg).

Step C—Synthesis of Compound 4

Aqueous formic acid (5 mL, 80%) was added to compound 4b (30 mg) followed by 100 µL HCl (4M in dioxane) and the resulting reaction was allowed to stir at room temperature for about 15 hours. The reaction mixture was then concentrated in vacuo and purified using flash column chromatography on silica gel using 0 to 20% methanol/dichloromethane to provide compound 4 (8.2 mg). LC/MS=606.2.

Example 5

Preparation of Compound 5

Step A—Synthesis of Compound 5a

A dry, N₂ flushed 500 mL round bottom flask was charged with compound 1e (5.0 g, 1.0 eq) and dry THF (100 mL). To this solution was sequentially added 4-nitrobenzoic acid (7.19 g, 2.0 eq), triphenylphosphine (11.29 g, 2.0 eq), and DIAD (8.48 mL, 2.0 eq) and the resulting reaction was allowed to stir a room temperature for 18 hours. The reaction mixture was then concentrated in vacuo and the resulting residue was purified using 0-60% EtOAc/hexanes to provide 7.77 g of 5a.

Step B—Synthesis of Compound 5b

To a solution of compound 5a (7.74 g) in dry THF (234 mL) was added aqueous 1N NaOH (107 mL). The biphasic mixture was stirred vigorously for 6.5 hours, then EtOAc (1200 mL) was added and the resulting solution was stirred vigorously for 30 minutes. The reaction mixture was separated and the organic layer was reserved while the aqueous layer was back extracted with EtOAc (2×300 mL). The original organic phase and the organic extracts were combined, dried over sodium sulfate, and filtered. The filtrate was treated with 1N NaOH(aq) and stirred vigorously for 30 minutes. The layers were separated, the aqueous layer was back extracted with EtOAc (200 mL), all organic layers were combined, dried over sodium sulfate, filtered, and concentrated in vacuo to provide compound 5b (4.67 g).

Step C—Synthesis of Compound 5

Compound 5b was converted to compound 5 using the methods described in Example 1, Steps E-J. LC/MS=272.25.

Example 6

Preparation of Compound 6

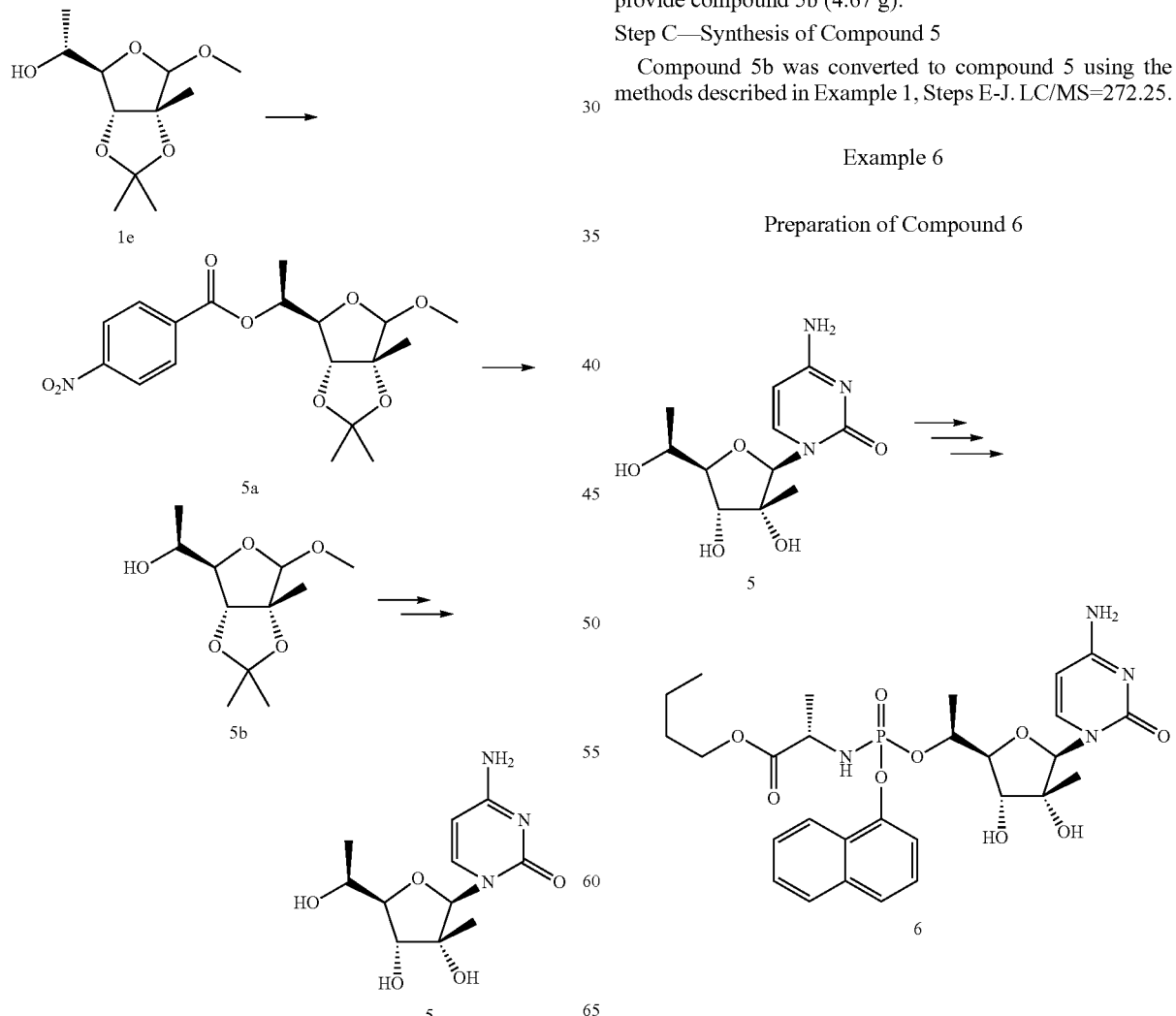

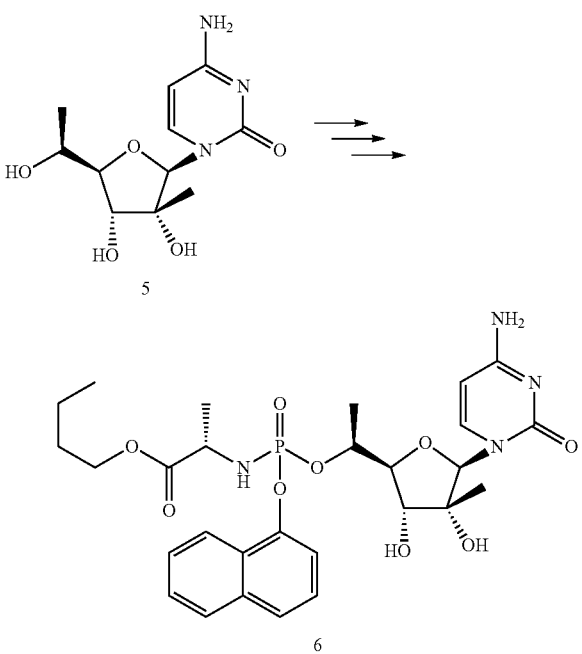

Compound 5 was converted to compound 6 using the methods described in Example 4, Steps A-C. LC/MS=605.2.

Example 7

Preparation of Compound 7

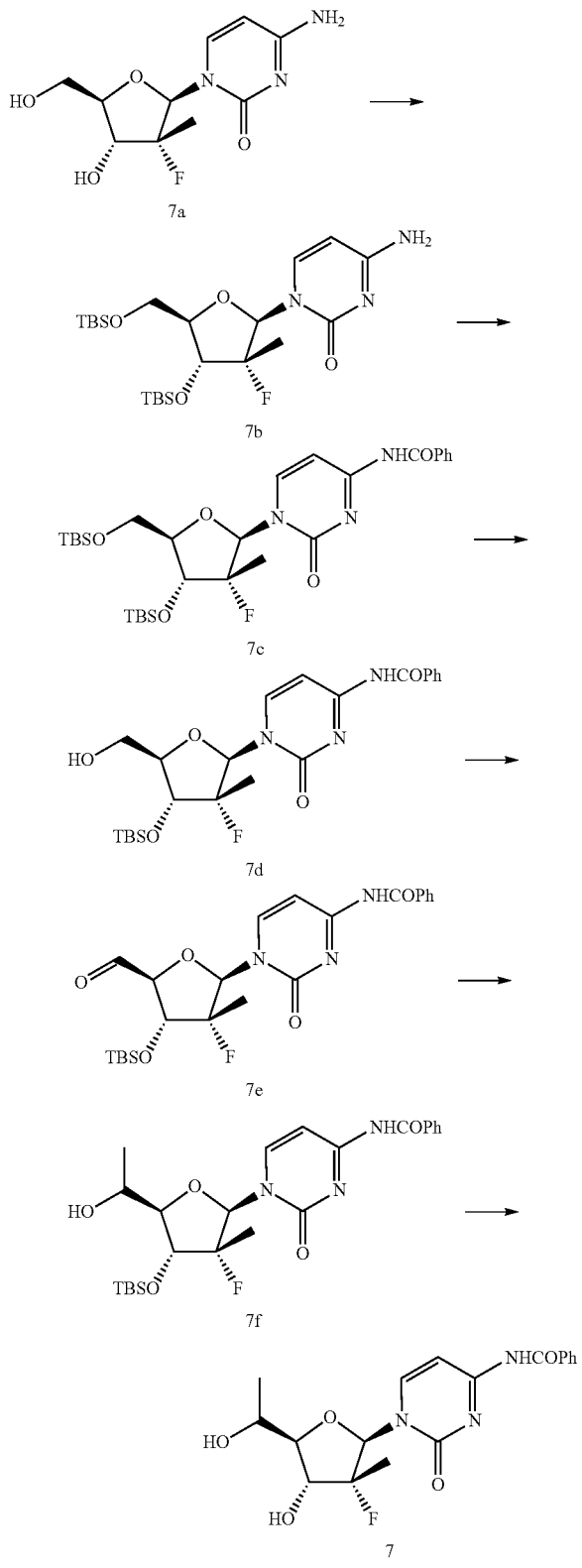

Step A—Synthesis of Compound 7b

To compound 7a (870 mg) in DMF (50 mL) was added imidazole (3.45 g), TBS-Cl (2.58 g) and catalytic DMAP (few crystals). The mixture was heated to 80° C. and allowed to stir at this temperate for about 15 hours. The reaction mixture was cooled to room temperature, diluted with EtOAc (300 mL) and water (250 mL). The organic phase was collected and the aqueous phase was extracted with EtOAc (200 mL). The combined organic phases were washed with water (300 mL), brine (300 mL), dried over sodium sulfate, filtered and concentrated in vacuo. The resulting residue was purified on a prepacked silica cartridge using 0/100 to 10/90 (35 min) methanol/$CH_2Cl_2$ to provide compound 7b (400 mg) as a white solid.

Step B—Synthesis of Compound 7c

A solution of compound 7b (400 mg) in pyridine (25 mL) was placed under nitrogen atmosphere and DMAP (few crystals) was added, followed by dropwise addition of benzoyl chloride (0.476 mL). The resulting reaction was allowed to stir at room temperature for about 15 hours, then the reaction mixture was diluted with EtOAc (200 mL) and saturated aqueous $NH_4Cl$ (200 mL). The solution was separated and the aqueous phase was extracted with EtOAc (150 mL). The combined organic phases were washed with aqueous 1N HCl (2×200 mL), brine (200 mL), dried over sodium sulfate, filtered and concentrated in vacuo. The resulting residue was purified on a prepacked silica cartridge using 0/100 to 60/40 EtOAc/hexanes to provide compound 7c (234 mg) as a white solid.

Step C—Synthesis of Compound 7d

To a solution of compound 7c (240 mg) in THF (4 mL) at 0° C. was added water (1 mL). After about 1 minute, TFA (1 mL) was added dropwise and the reaction mixture was slowly warmed to room temperature, with stirring, over 5 hours. The reaction mixture was then cooled to 0° C., and EtOAc (50 mL) and saturated aqueous $NaHCO_3$ (50 mL) were added. The solution was separated and the aqueous layer was extracted with EtOAc (50 mL). The combined organic phases were washed with saturated aqueous $NaHCO_3$ (50 mL), brine (50 mL), dried over sodium sulfate, filtered and concentrated in vacuo. The resulting residue was purified on a prepacked silica cartridge using 0/100 to 60/40 of EtOAc/hexanes to provide 150 mg. (white solid) of 7d.

Step D—Synthesis of Compound 7e

A solution of compound 7d (70 mg) in $CH_2Cl_2$ (10 mL) was placed under nitrogen atmosphere and Dess-Martin periodinane (186 mg) was added in one bulk addition. The resulting reaction was allowed to stir for 2 hours, then the reaction mixture was diluted with EtOAc (25 mL), followed by saturated aqueous $NaHCO_3$ (15 mL) and saturated aqueous $Na_2S_2O_3$ solution (15 mL). The resulting solution was allowed to stir for 5 minutes, then was separated. The aqueous layer was extracted with EtOAc (25 mL) and the combined organic phases were washed with saturated aqueous $NaHCO_3$ (15 mL)/saturated aqueous $Na_2S_2O_3$ solution (15 mL), brine (30 mL), dried over sodium sulfate, filtered and concentrated in vacuo. The residue obtained was azeotroped with toluene (10 mL) to provide compound 7e, which was used without further purification.

Step E—Synthesis of Compound 7f

Compound 7e was taken up in THF (2 mL), and cooled to −78° C. under nitrogen atmosphere. MeMgBr (3M in ether, 0.24 mL) was added dropwise and the resulting reaction was allowed to stir for 5 hours, during which time the temperature increased to about 10° C. The reaction was quenched with saturated aqueous $NH_4Cl$ (25 mL) and extracted with EtOAc (2×25 mL). The combined organic extracts were washed with saturated aqueous $NH_4Cl$ (25 mL), brine (25 mL), dried over sodium sulfate, filtered and concentrated in vacuo. The residue obtained was purified on a prepacked silica cartridge using 0/100 to 70/30 of EtOAc/hexanes to provide compound 7f (22.5 mg) as a white solid.

Step F—Synthesis of Compound 7

A solution of compound 7f (22 mg) in THF (1.5 mL) was cooled to 0° C. and to the cooled solution was added TBAF (1M in THF, 0.067 mL) dropwise. The resulting reaction was allowed to stir at 0° C. for 1 hour, then stirred for an additional 15 hours with the temperature maintained at about 5° C. The reaction was quenched with saturated aqueous NH$_4$Cl (30 mL), and extracted into EtOAc (2×30 mL). The combined organic extracts were washed with brine (30 mL), dried over sodium sulfate, filtered and concentrated in vacuo. The residue obtained was purified on a prepacked silica cartridge using 0/100 to 15/85 of methanol/CH$_2$Cl$_2$ to provide compound 7 in quantitative yield. LC/MS=378.14.

Example 8

Preparation of Compound 8

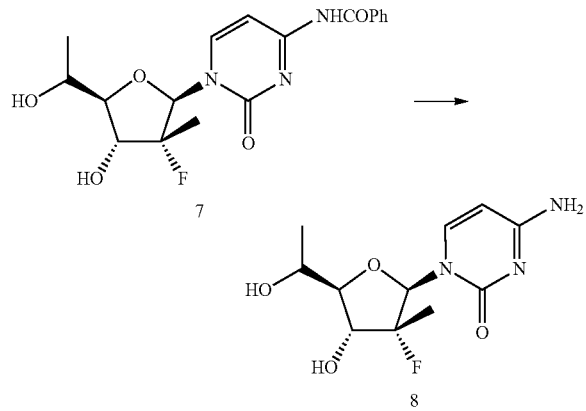

To a solution of compound 7 (14 mg) in THF (1 mL) was added 7N NH$_3$ in methanol (2 mL). The resulting reaction was allowed to stir at room temperature for about 15 hours, then the reaction mixture was concentrated in vacuo. The resulting residue was purified on a prepacked silica cartridge using 0/100% to 15/85% of 7N NH$_3$ in methanol/CH$_2$Cl$_2$ to provide compound 8 (7 mg). LC/MS=274.12.

Example 9

Preparation of Compound 9

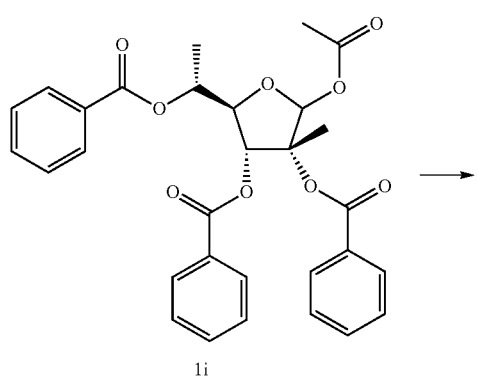

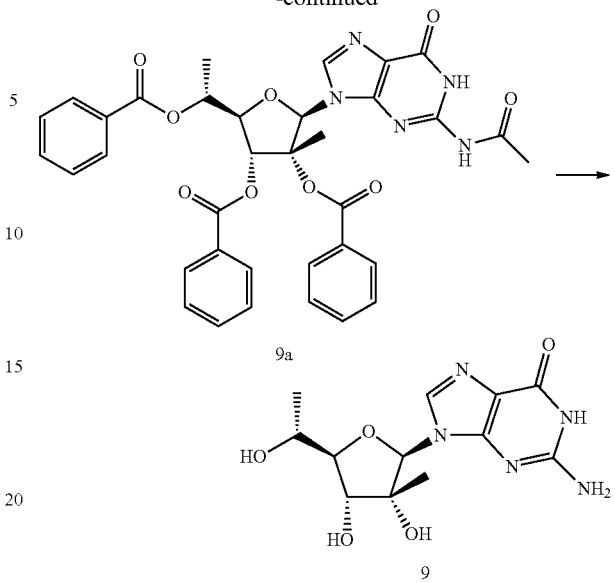

Step A—Synthesis of Compound 9a

Compound 1i (300 mg, 0.54 mmol) was taken up in acetonitrile (20 mL) and to the resulting solution was added N-(6-oxo-6,9-dihydro-1H-purin-2-yl)acetamide (330 mg, 1.6 mmol), followed by bis(trimethylsilyl)acetimide (775 μL, 3.4 mmol). The reaction was heated to 90° C. and allowed to stir at this temperature for 30 minutes. The reaction mixture was then cooled to 0° C. and TMSOTf (360 μL, 1.9 mmol) was added dropwise. The resulting reaction was allowed to warm to room temperature and then was heated to 90° C. and allowed to stir at this temperature for about 15 hours. The reaction mixture was quenched with NaHCO$_3$ and extracted with CHCl$_3$ (3×20 mL) and the combined organic extracts were dried over MgSO$_4$, filtered and concentrated in vacuo. The resulting residue was purified using flash column chromatography on silica gel using 0-100% EtOAc/hexanes to provide compound 9a (100 mg).

Step B—Synthesis of Compound 9

Compound 9a was taken up in 7N NH$_3$ in methanol (5 mL) and NH$_4$OH (1 mL) and the resulting reaction heated to 90° C. and allowed to stir at this temperature for about 15 hours. The reaction mixture was cooled to room temperature, concentrated in vacuo, and the resulting residue was purified using flash column chromatography on silica gel using 0 to 20% methanol/EtOAc to provide compound 9 (15 mg). LC/MS=312.2

Example 10

Preparation of Compound 10

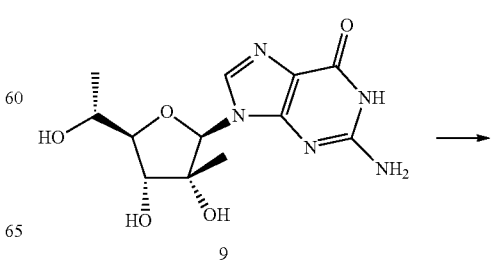

53

-continued

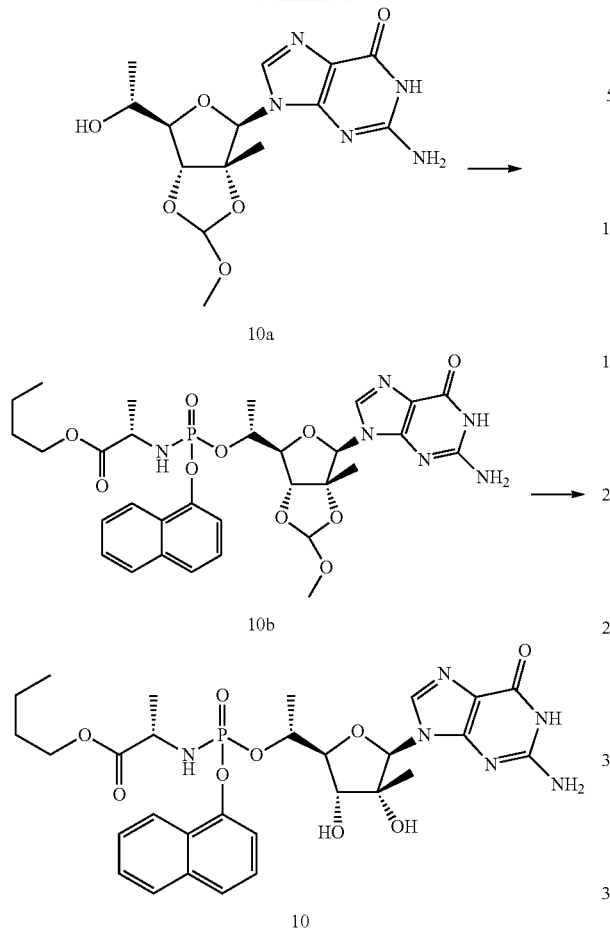

10a

10b

10

Step A—Synthesis of Compound 10a

Compound 9 was taken up in dioxane (5 mL) and to the resulting solution was added (MeO)₃CH (3 mL), followed by p-TsOH (90 mg). The resulting reaction was allowed to stir at room temperature for about 15 hours, then the reaction was cooled to 0° C. and triethylamine (100 µL) was added. The resulting solution was concentrated in vacuo and the resulting residue was purified using flash column chromatography on silica gel using 0 to 20% methanol/EtOAc to provide compound 10a (30 mg) as a mixture of diastereomers, which was used without further purification.

Step B—Synthesis of Compound 10b

Compound 10a (30 mg) was converted to compound 10b (50 mg) using the method described above in Example 4, Step B.

Step C—Synthesis of Compound 10

Aqueous formic acid (5 mL, 80%) was added to compound 10b (50 mg), followed by 100 µL HCl (4M in dioxane) and the resulting reaction was allowed to stir at room temperature for about 15 hours. The reaction mixture was then concentrated in vacuo and the residue obtained was purified using flash column chromatography on silica gel using 0 to 20% methanol/dichloromethane to provide compound 10 (24.7 mg, 53%). LC/MS=645.2.

54

Example 11

Preparation of Compound 11

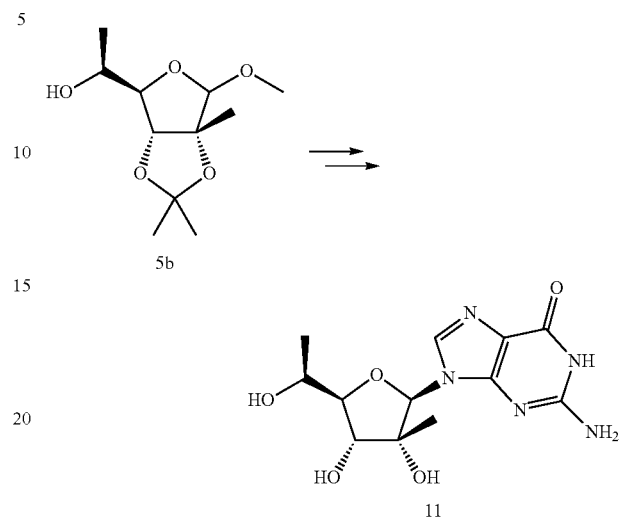

5b

11

Compound 5b was converted to 11 using the methods described in Example 1, Steps E-H and Example 9, Steps A and B. LC/MS=312.07.

Example 12

Preparation of Compound 12

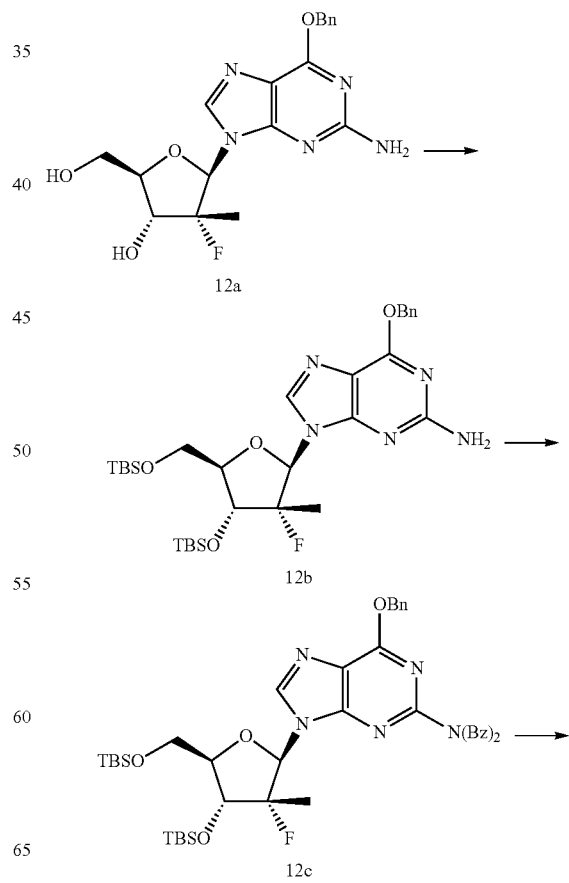

12a

12b

12c

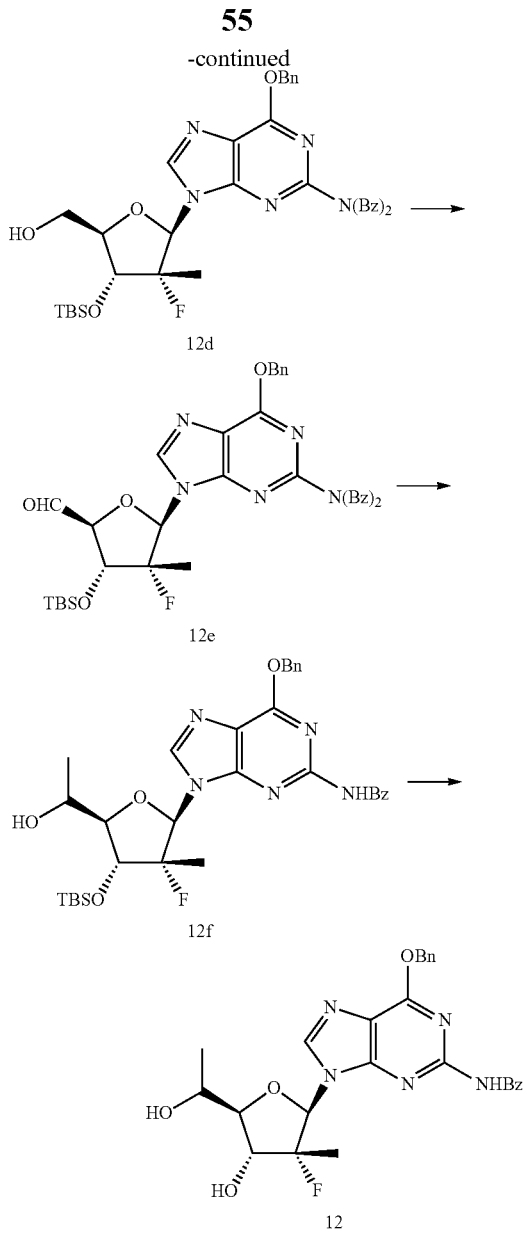

Step A—Synthesis of Compound 12b

To a solution of compound 12a (5 g) (prepared using methods described in International Publication No. WO 09/152,095) in pyridine (15 mL) was added TBSCl (2.5 eq) under $N_2$ atmosphere at room temperature. The reaction was allowed to stir for 18 hours, then the reaction mixture was concentrated in vacuo. The residue obtained was dissolved in EtOAc and the resulting solution was diluted with water. The collected organic phase was dried over $MgSO_4$, filtered and concentrated in vacuo and the resulting residue was purified on a packed silica gel cartridge using a gradient of from 0% to 60% EtOAc/hexanes to provide compound 12b (50%).

Step B—Synthesis of Compound 12c

To a solution of compound 12b (50 mg) in pyridine (1 mL) under $N_2$ atmosphere was added benzoyl chloride (1.5 eq). The resulting reaction was allowed to stir at room temperature for about 15 hours, then the reaction mixture was concentrated in vacuo. The residue obtained was dissolved in EtOAc and the resulting solution was diluted with water. The collected organic phase was dried over $MgSO_4$, filtered and concentrated in vacuo and the resulting residue was purified on a packed silica gel cartridge using a gradient of from 0% to 40% EtOAc/hexanes to provide compound 12c (35%).

Step C—Synthesis of Compound 12d

A solution of compound 12c (0.02 g) in 1 mL of THF was cooled to 0° C. and to the cooled solution was added 1 mL of $TFA/H_2O$ (1:1). The reaction mixture was allowed to stir at 0° C. for 3 hours, then the reaction was quenched with saturated aqueous $NaHCO_3$ and extracted with ethyl acetate (3×3 mL). The combined organic extracts were dried over $MgSO_4$, filtered and concentrated in vacuo. The resulting residue was purified using flash column chromatography on silica gel (0% to 60% EtOAc/hexanes) to provide compound 12d (43%).

Step E—Synthesis of Compound 12e

Compound 12d (0.020 g) was taken in 5 mL of anhydrous dichloromethane under N2 atmosphere and stirred at room temperature. Dess-Martin periodinane (0.030 g, 2.5 eq) was added and the resulting reaction was allowed to stir for 1 hour, then the reaction was quenched with 1 mL of sat'd $NaHCO_3$ and 1 mL of sodium thiosulfate. The resulting solution was extracted with dichloromethane, the organic extract was washed with brine, dried over $MgSO_4$, filtered and concentrated in vacuo to provide 100% crude yield of 12e, which was used without further purification.

Step F—Synthesis of Compound 12f

A solution of compound 12e (0.098 g) in 2 mL of THF was placed under nitrogen atmosphere and cooled to −78° C. A −78° C. solution of $CH_3MgBr$ in diethylether (0.23 ml, 5.0 eq) was added and the reaction was allowed to stir for 5 hours, during which time the temperature raised to about 10° C. The reaction mixture was quenched with saturated aqueous $NH_4Cl$ and diluted with $H_2O$. The resulting solution was extracted with EtOAc (3×3 mL) and the combined organic extracts were dried over $MgSO_4$, filtered and concentrated in vacuo. The residue obtained was purified using reverse phase HPLC (Varian Dynamax HPLC system, with Luna C-18, 21×250 mm, 5 um column. Gradient—5% to 60% to 100% to 5% $CH_3CN$—$H_2O$) to provide compound 12f (0.030 g, 22%).

Step G—Synthesis of Compound 12

A solution of compound 12f (0.004 g) in THF (0.5 mL) was placed under nitrogen atmosphere, then TBAF (0.01 mL, 1M in THF) was added and the resulting reaction was allowed to stir for 4 hours. The reaction mixture was concentrated in vacuo and the residue obtained was purified using reverse phase HPLC (described above in Step F, gradient—5% to 60% $CH_3CN$—$H_2O$) to provide compound 12 (2.2 mg, 47%). LC/MS=508.2.

Example 13

Preparation of Compound 13

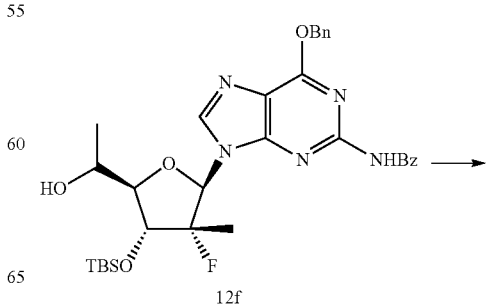

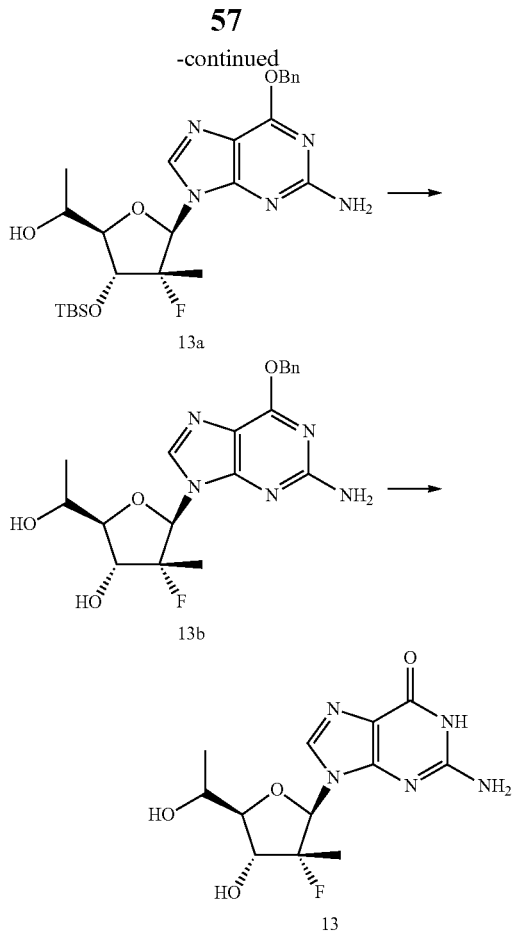

Step A—Synthesis of Compound 13a

A solution of 12f (21.4 mg) in 5 mL of ammonia in methanol (7N) was placed in a sealed tube at room temperature. The reaction was heated to 100° C. for 5 h. The reaction mixture was then concentrated in vacuo and the residue obtained was purified using reverse phase HPLC (conditions described above in Example 13, Step F) to provide 13a (9 mg, 51%).

Step B—Synthesis of Compound 13b

To a solution of compound 13a (9 mg) in 0.50 mL of anhydrous THF was added TBAF (0.026 mL, 1M in THF) at room temperature. The reaction was allowed to stir for about 4 hours, then the reaction mixture was concentrated in vacuo to provide compound 13b, which was used without further purification.

Step C—Synthesis of Compound 13

Compound 13b (3.50 mg) was taken in 3.0 mL of EtOH and to the resulting solution was added 10% Pd/C (1 mg). The reaction flask was evacuated and the reaction was put under hydrogen atmosphere using a $H_2$-filled balloon. The reaction was allowed to stir for 2 hours at room temperature, then was filtered through a short pad of Celite. The filtrate was concentrated in vacuo and the resulting residue was purified using reverse phase HPLC (described above in Step G) to provide compound 13 (1.6 mg, 59%). LC/MS=314.12.

Example 14

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 μM to 1 μM. The final concentration of dimethylsulfoxide was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ ID. NO. 1); 5B.2R, TTGATGGGCAGCTTGGTTTC (SEQ ID. NO. 2); the probe sequence was FAM-labeled CACGCCATGCGCTGCGG (SEQ ID. NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minute. The ACT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV replicon data ($EC_{50}$) was measured for the compounds of the present invention and the data obtained is provided in the table below.

| Compound | 1b $EC_{50}$ (μM) |
| --- | --- |
| 1 | >100 |
| 2 | 10 |
| 3 | >100 |
| 4 | >100 |
| 5 | >100 |
| 6 | >100 |
| 7 | >100 |
| 8 | 38 |
| 9 | >100 |
| 10 | >100 |
| 11 | >100 |
| 12 | 14 |
| 13 | 3.5 |

Uses of the 5'-Substituted Nucleoside Analogs

The 5'-Substituted Nucleoside Analogs are useful in human and veterinary medicine for treating or preventing a viral infection in a patient. In one embodiment, the 5'-Substituted Nucleoside Analogs can be inhibitors of viral replication. In another embodiment, the 5'-Substituted Nucleoside Analogs can be inhibitors of HCV replication. Accordingly, the 5'-Substituted Nucleoside Analogs are useful for treating viral infections, such as HCV. In accordance with the invention, the 5'-Substituted Nucleoside Analogs can be administered to a patient in need of treatment or prevention of a viral infection.

Accordingly, in one embodiment, the invention provides methods for treating a viral infection in a patient comprising administering to the patient an effective amount of at least one 5'-Substituted Nucleoside Analog or a pharmaceutically acceptable salt thereof.

Treatment or Prevention of a Flaviviridae Virus

The 5'-Substituted Nucleoside Analogs can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The 5'-Substituted Nucleoside Analogs are useful in the inhibition of HCV, the treatment of HCV infection and/or reduction of the likelihood or severity of symptoms of HCV infection and the inhibition of HCV viral replication and/or HCV viral production in a cell-based system. For example, the 5'-Substituted Nucleoside Analogs are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one 5'-Substituted Nucleoside Analog or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The 5'-Substituted Nucleoside Analogs are also useful in the preparation and execution of screening assays for antiviral compounds. For example the 5'-Substituted Nucleoside Analogs are useful for identifying resistant HCV replicon cell lines harboring mutations within NS5B, which are excellent screening tools for more powerful antiviral compounds. Furthermore, the 5'-Substituted Nucleoside Analogs are useful in establishing or determining the binding site of other antivirals to the HCV NS5B polymerase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Ptl):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not 5'-Substituted Nucleoside Analogs.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 5'-Substituted Nucleoside Analog (which may include two or more different 2'-Substituted Nucleoside Derivatives), or a pharmaceutically acceptable salt thereof, and (ii) at least one additional therapeutic agent that is other than a 5'-Substituted Nucleoside Analog, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 5'-Substituted Nucleoside Analog and an additional therapeutic agent may be present in fixed amounts (dosage amounts) in a single dosage unit (e.g., a capsule, a tablet and the like).

In one embodiment, the at least one 5'-Substituted Nucleoside Analog is administered during a time when the additional therapeutic agent(s) exert their prophylactic or therapeutic effect, or vice versa.

In another embodiment, the at least one 5'-Substituted Nucleoside Analog and the additional therapeutic agent(s) are administered in doses commonly employed when such agents are used as monotherapy for treating a viral infection.

In another embodiment, the at least one 5'-Substituted Nucleoside Analog and the additional therapeutic agent(s) are administered in doses lower than the doses commonly employed when such agents are used as monotherapy for treating a viral infection.

In still another embodiment, the at least one 5'-Substituted Nucleoside Analog and the additional therapeutic agent(s) act synergistically and are administered in doses lower than the doses commonly employed when such agents are used as monotherapy for treating a viral infection.

In one embodiment, the at least one 5'-Substituted Nucleoside Analog and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one 5'-Substituted Nucleoside Analog and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one 5'-Substituted Nucleoside Analog and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), PSI-7977 (Pharmasset), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (WyethNirroPharma), HCV-796 (WyethNiroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development,* 7(4):446 (2004); Tan et al., *Nature Reviews,* 1:867 (2002); and Beaulieu et al., *Current Opinion in Investigational Drugs,* 5:838 (2004).

Other HCV polymerase inhibitors useful in the present compositions and methods include, but are not limited to, those disclosed in International Publication Nos. WO 08/082,484, WO 08/082,488, WO 08/083,351, WO 08/136,815, WO 09/032,116, WO 09/032,123, WO 09/032,124 and WO 09/032,125; and the following compounds:

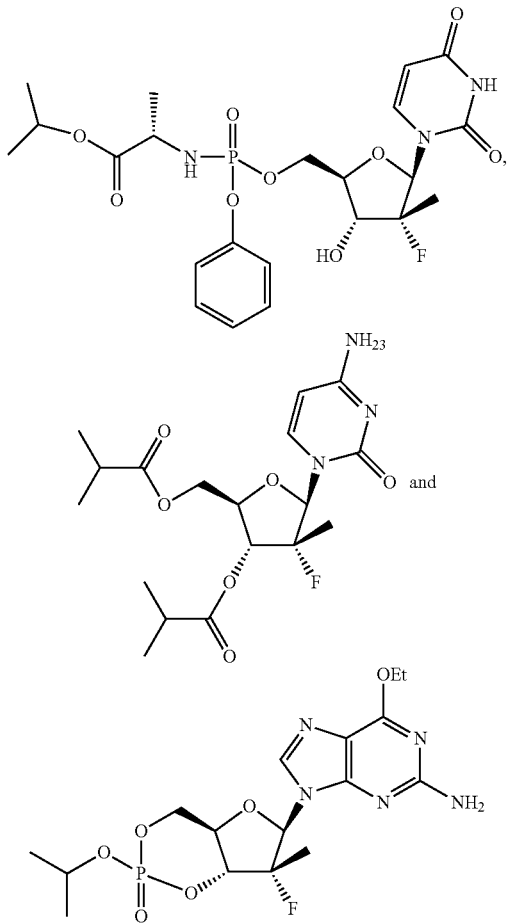

and pharmaceutically acceptable salts thereof.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

Additional HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, the following compounds:

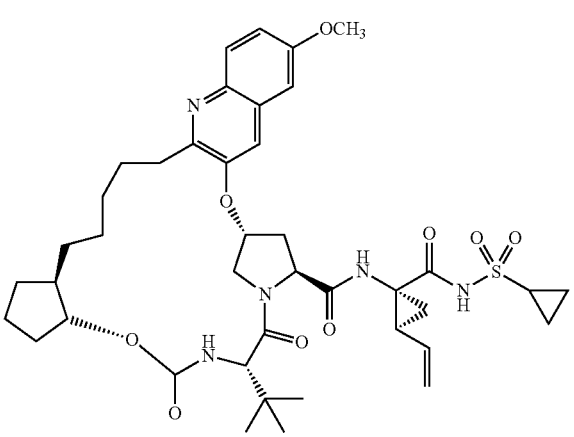

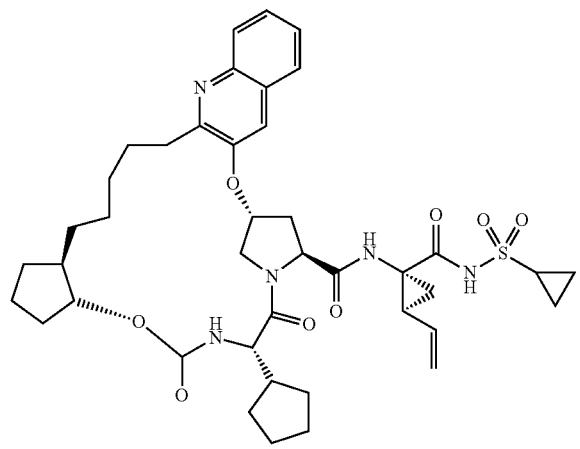
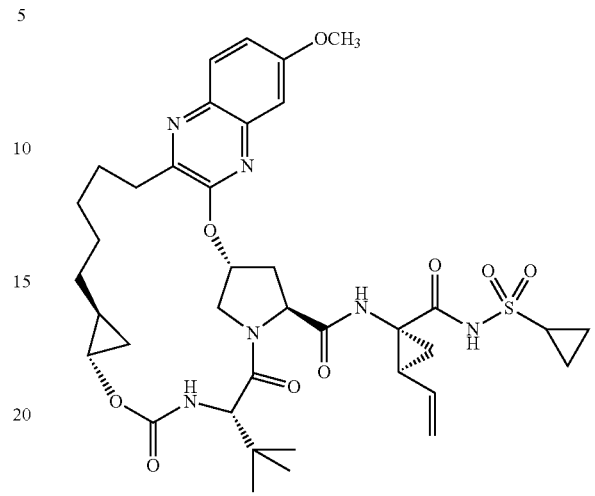
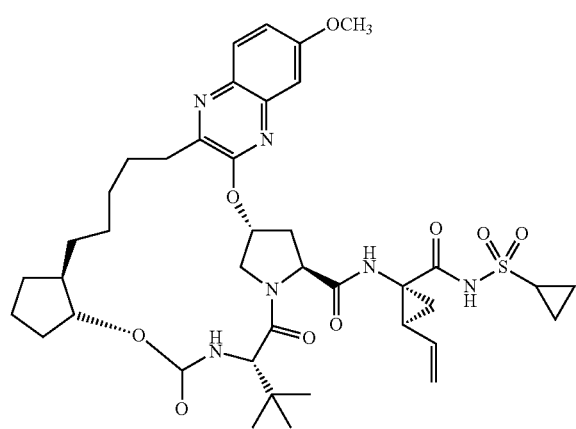
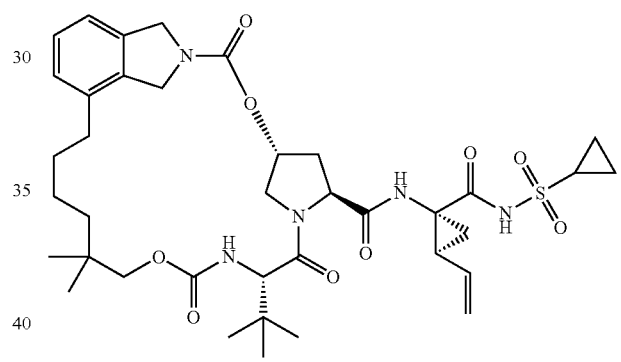
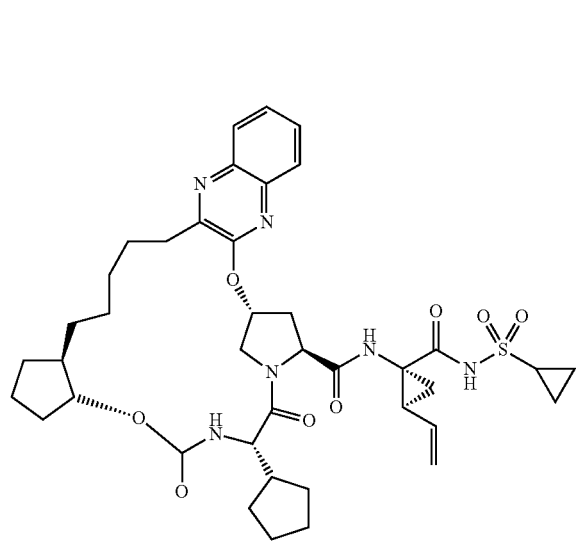
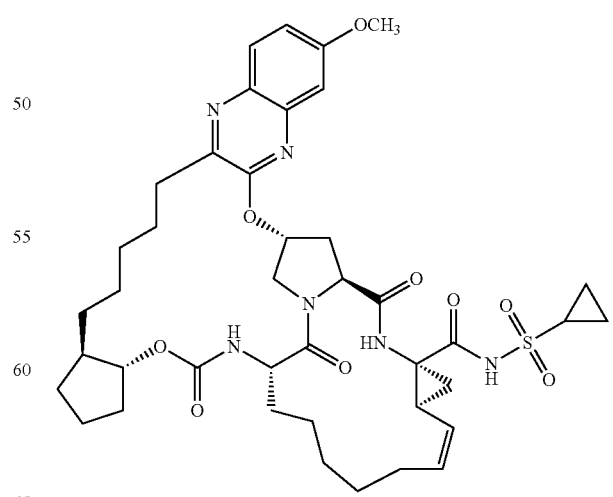

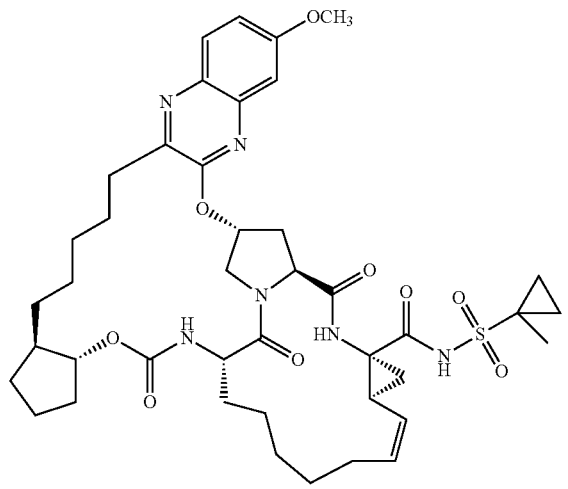
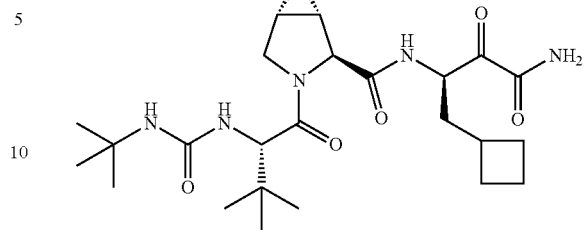
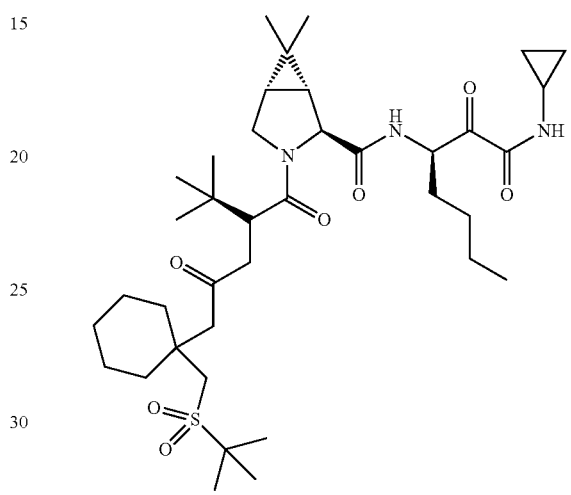
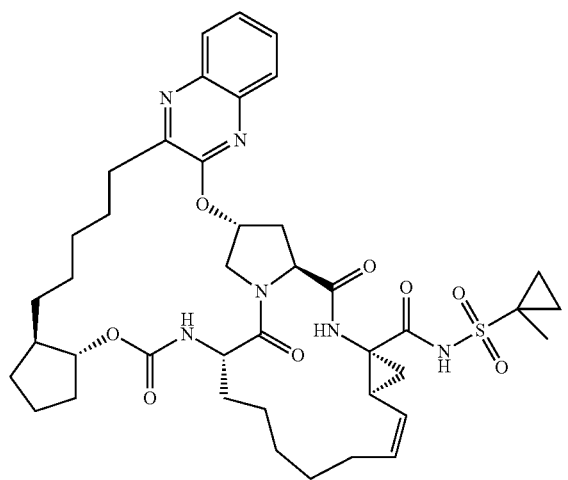
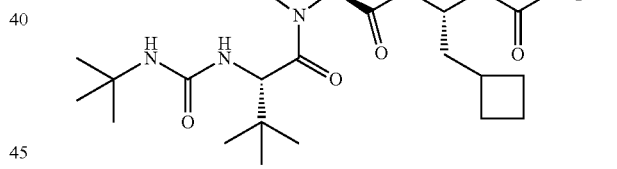
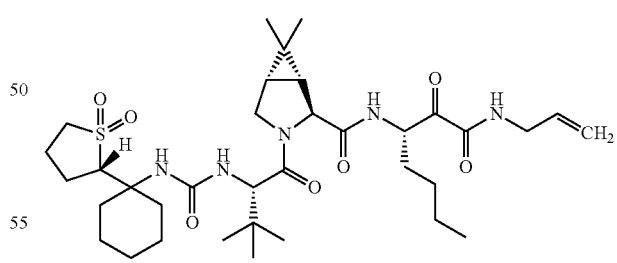
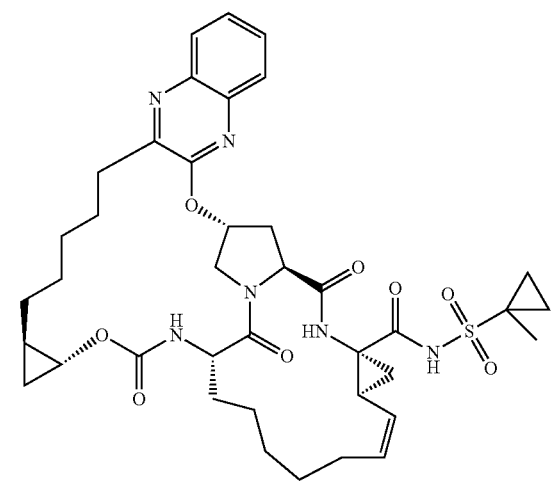
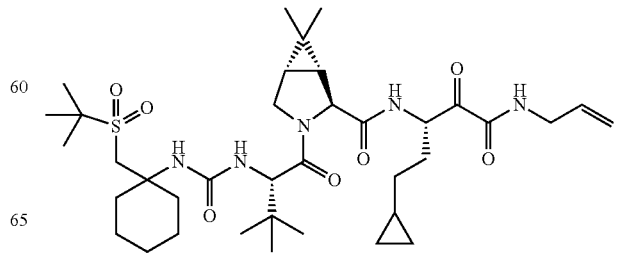

69
-continued
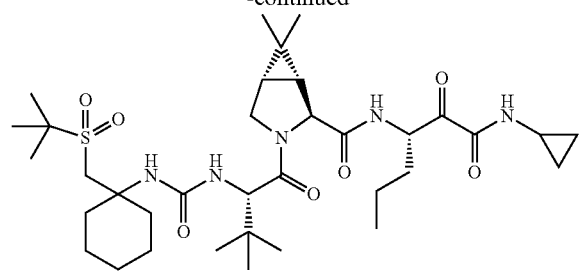
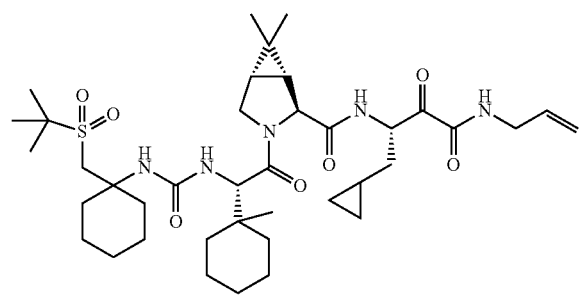
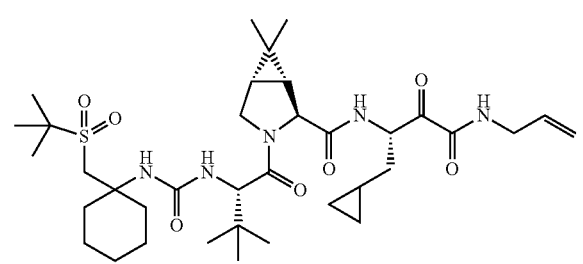
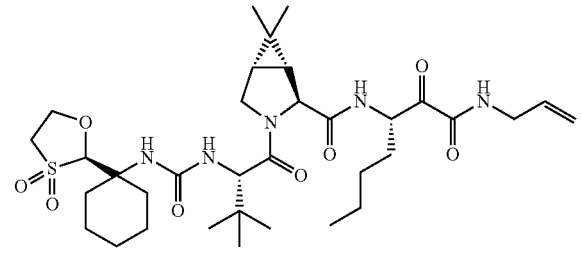
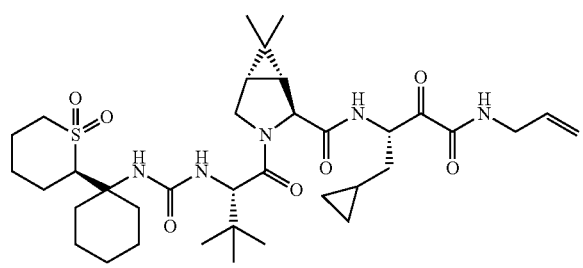
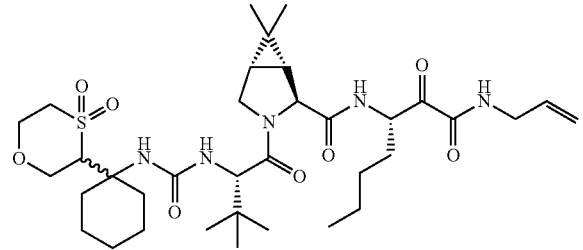
70
-continued
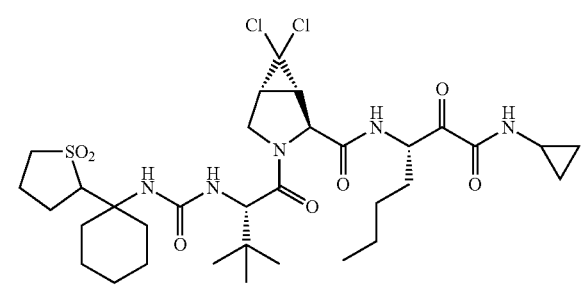
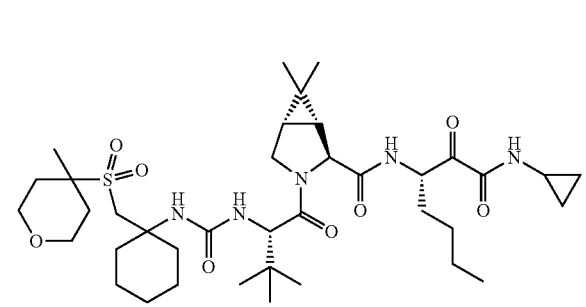
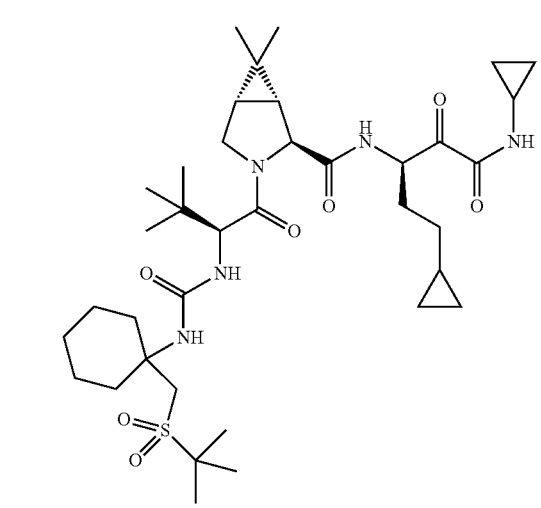
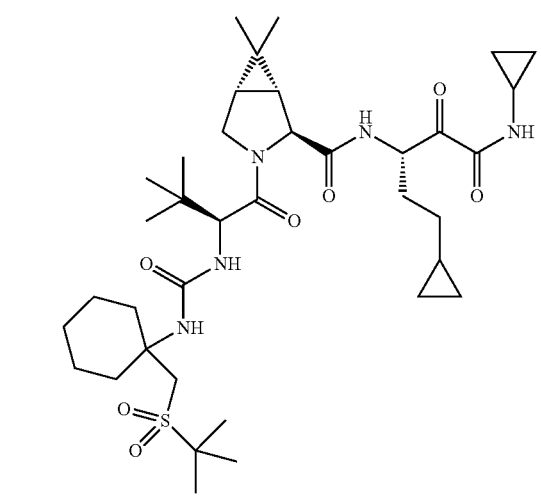

71

-continued

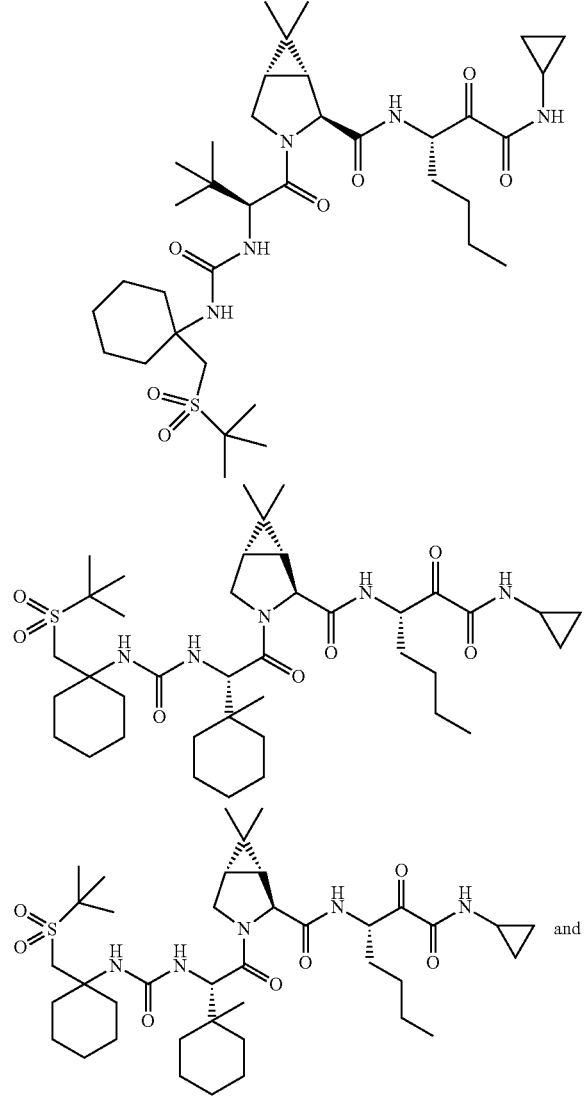

72

-continued

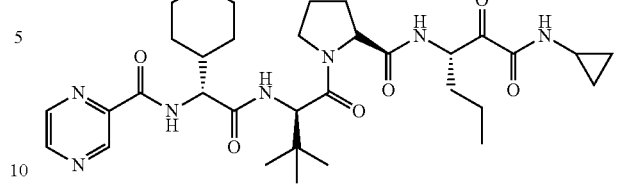

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

Viral entry inhibitors useful as second additional therapeutic agents in the present compositions and methods include, but are not limited to, PRO-206 (Progenics), REP-9C (REPI-Cor), SP-30 (Samaritan Pharmaceuticals) and ITX-5061 (iTherx).

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful as second additional therapeutic agents in the present compositions and methods include, but are not limited to, AZD2836 (Astra Zeneca), ACH-1095 (Achillion) and ACH-806 (Achillion).

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), PPI-461 (Presidio), PPI-1301 (Presidio), BMS-824383 (Bristol-Myers Squibb) and BMS-790052 (Bristol-Myers Squibb). Additional HCV NS4A inhibitors useful as second additional therapeutic agents in the present compositions and methods include, but are not limited to those disclosed in International Publication No. WO 2010/111483 and the following compounds:

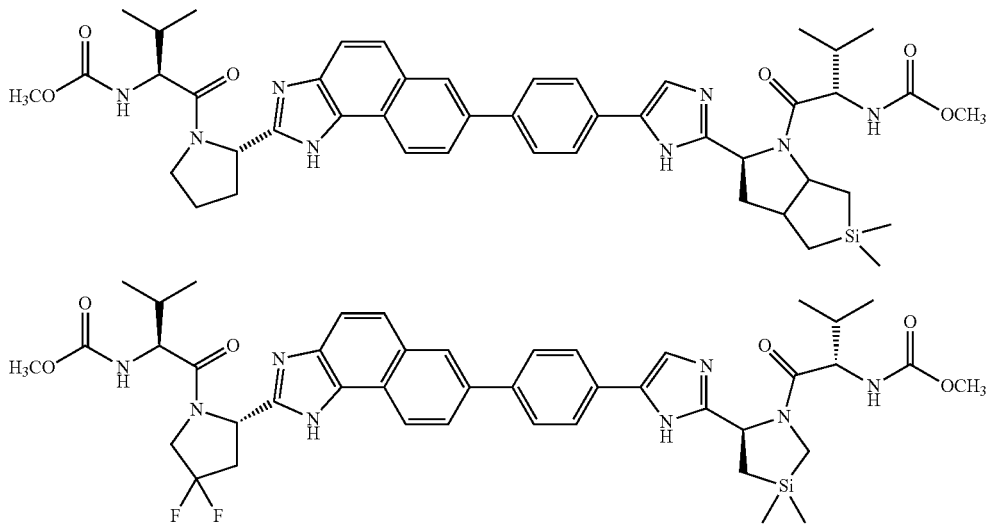

-continued
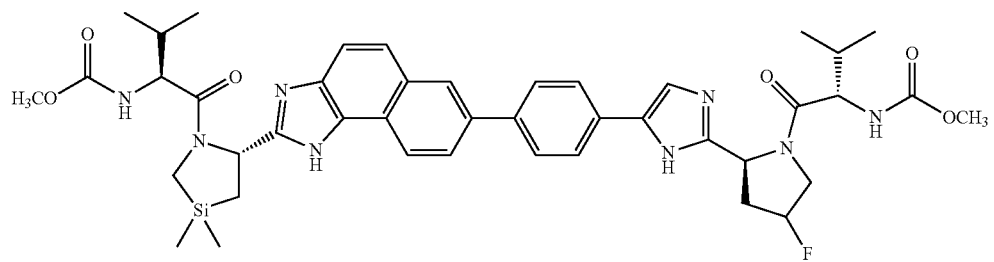
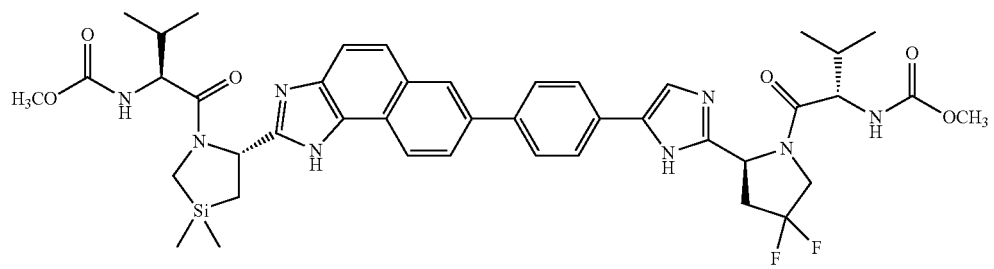
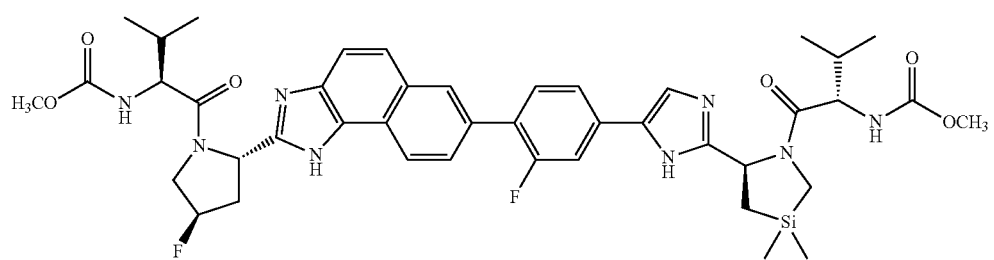
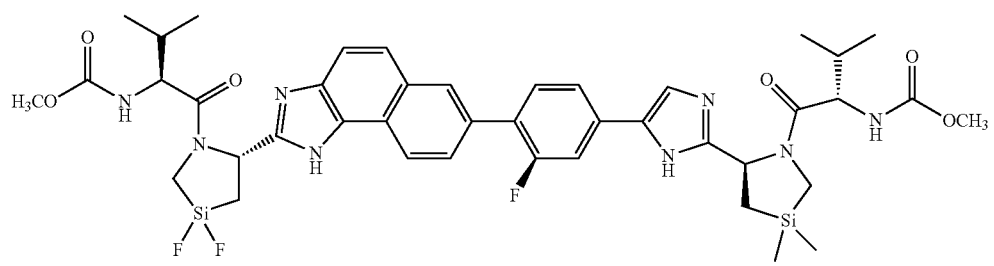
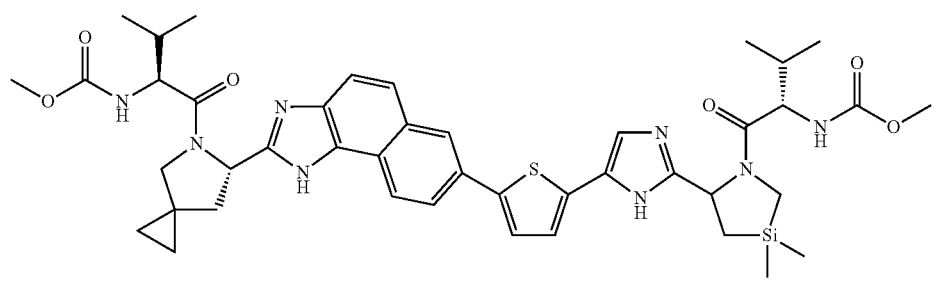
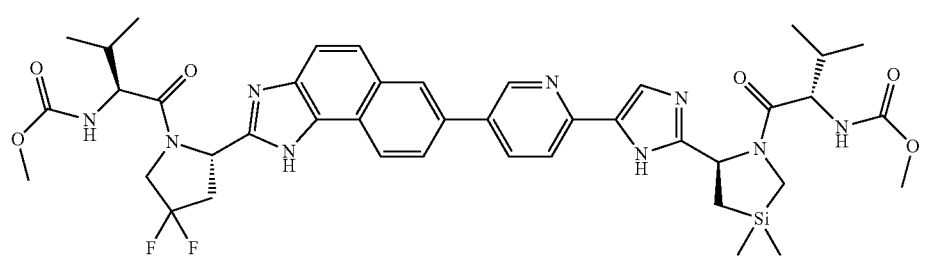

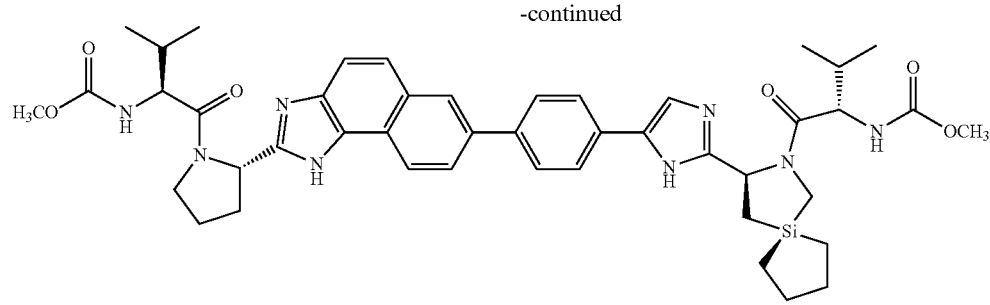
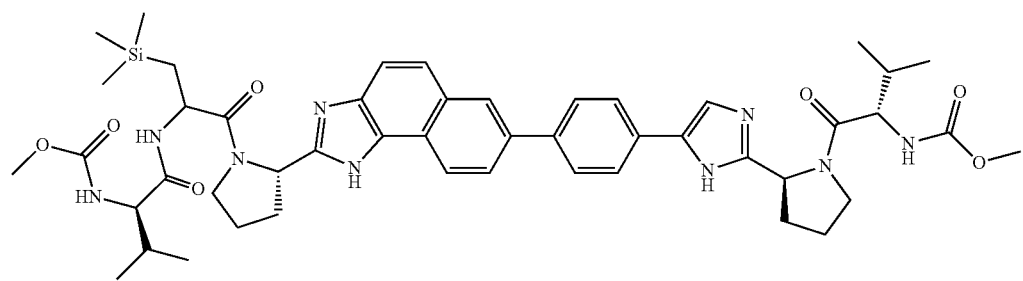
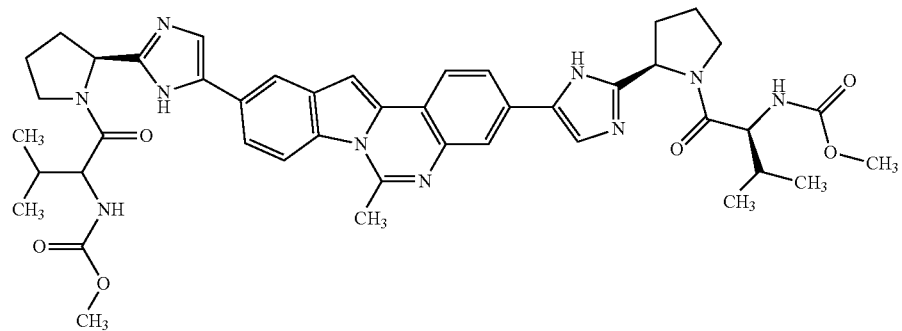
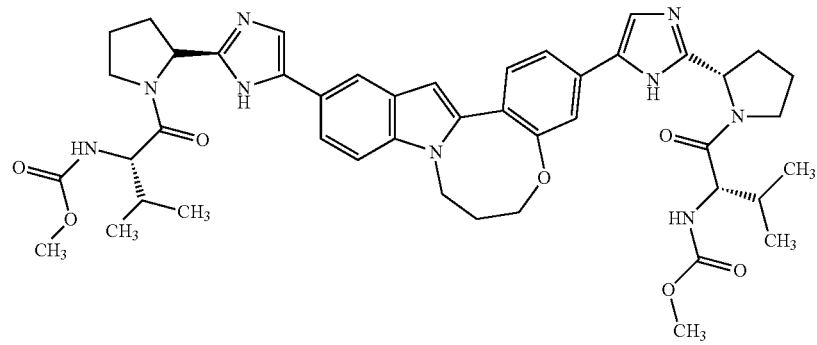
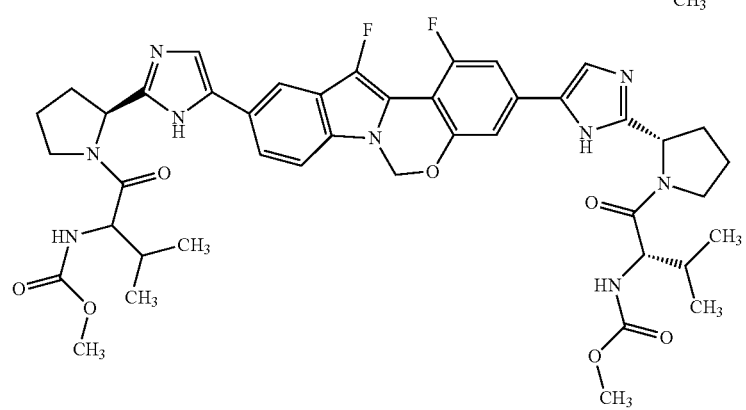

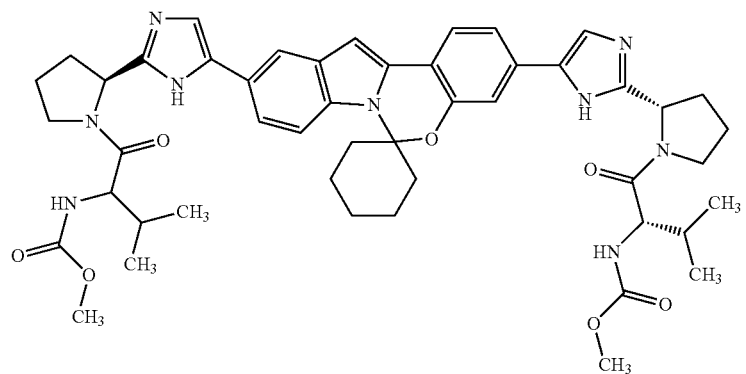
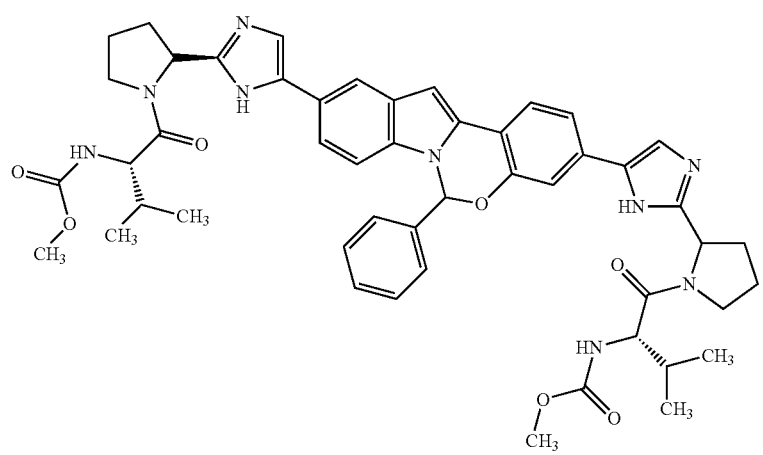
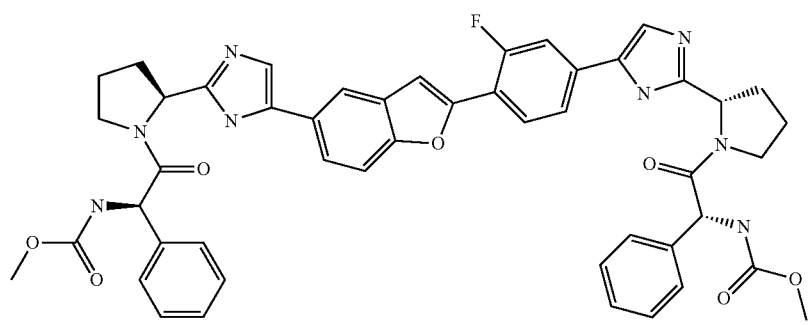
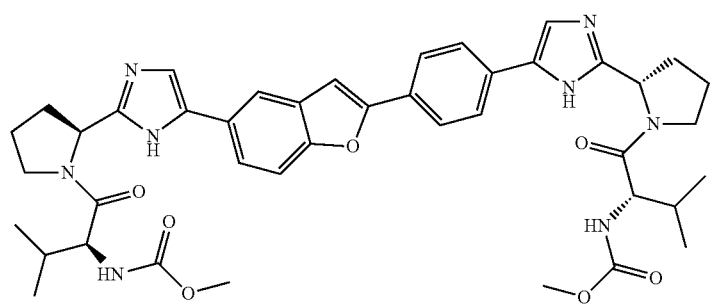

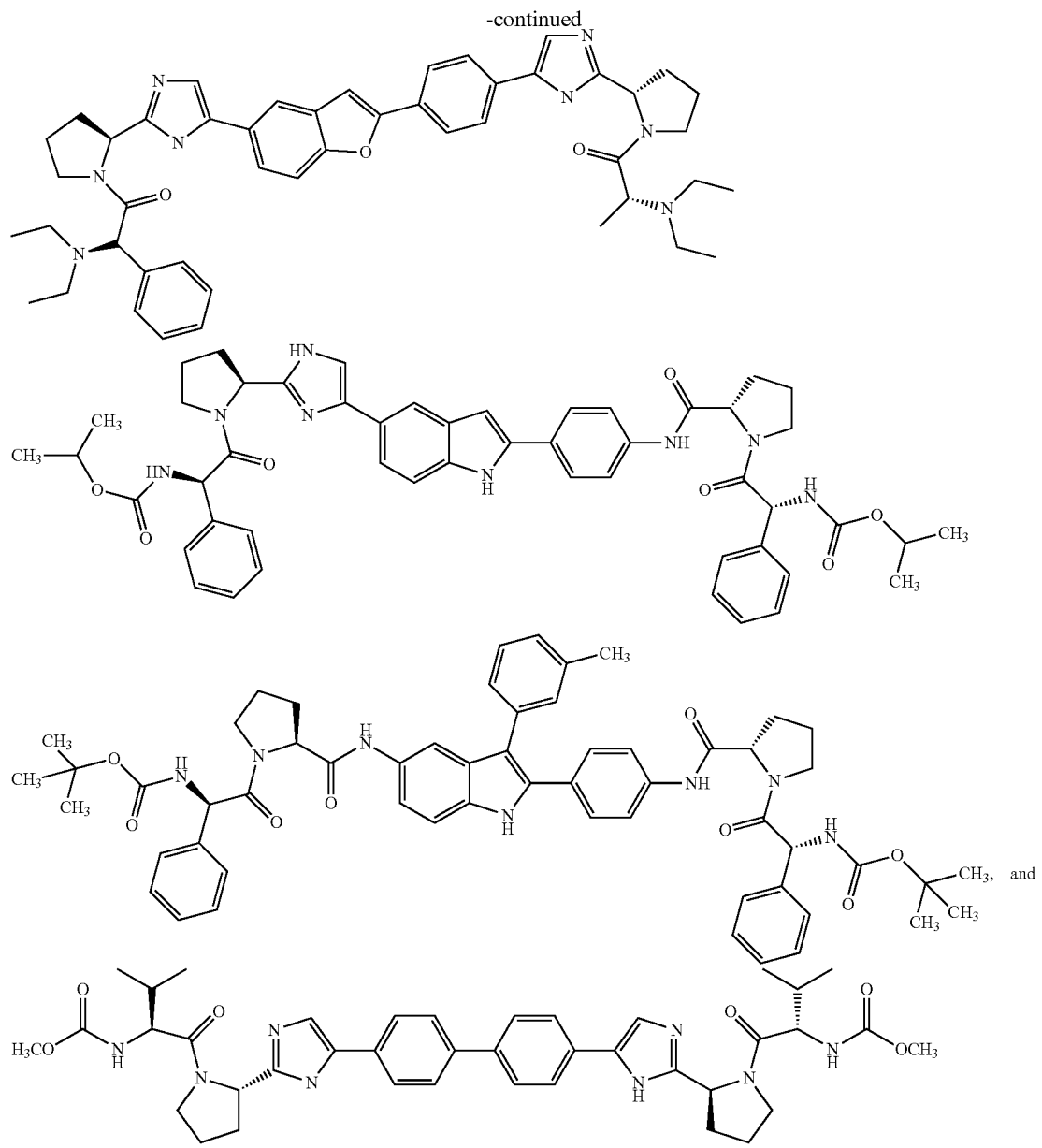

and pharmaceutically acceptable salts thereof.

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell/Novartis), CSL123 (Chiron/CSL), GI 5005 (Globeimmune), TG-4040 (Transgene), GNI-103 (GENimmune), HepavaxxC (ViRex Medical), ChronVac-C (Inovio/Tripep), PeviPRO™ (Pevion Biotect), HCV/MF59 (Chiron/Novartis), MBL-HCV1 (MassBiologics), GI-5005 (GlobeImmune), CT-011 (CureTech/Teva) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the 5'-Substituted Nucleoside Analog(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one 5'-Substituted Nucleoside Analog(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, an HCV NS5A inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the 5'-Substituted Nucleoside Analogs are useful in veterinary and human medicine. As described above, the 5'-Substituted Nucleoside Analogs are useful for treating or preventing HCV infection in a patient in need thereof.

When administered to a patient, the 5'-Substituted Nucleoside Analogs can be administered as a component of a composition that comprises a pharmaceutically acceptable carrier or vehicle. The present invention provides pharmaceutical compositions comprising an effective amount of at least one 5'-Substituted Nucleoside Analog and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 5'-Substituted Nucleoside Analogs are administered orally.

In another embodiment, the one or more 5'-Substituted Nucleoside Analogs are administered intravenously.

In one embodiment, a pharmaceutical preparation comprising at least one 5'-Substituted Nucleoside Analog is in unit dosage form. In such form, the preparation is subdivided into unit doses containing effective amounts of the active components.

Compositions can be prepared of conventional mixing, granulating or coating methods, respectively, and the present compositions can contain, in one embodiment, from about 0.1% to about 99% of the 5'-Substituted Nucleoside Analog(s) by weight or volume. In various embodiments, the present compositions can contain, in one embodiment, from about 1% to about 70% or from about 5% to about 60% of the 5'-Substituted Nucleoside Analog(s) by weight or volume.

The quantity of 5'-Substituted Nucleoside Analog in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 5'-Substituted Nucleoside Analogs will be regulated of the judgment of the attending clinician considering such factors as age, condition and size of the patient as well as severity of the symptoms being treated. Generally, a total daily dosage of the 5'-Substituted Nucleoside Analogs range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 5'-Substituted Nucleoside Analog or a pharmaceutically acceptable salt thereof; (ii) one or more additional therapeutic agents that are not a 5'-Substituted Nucleoside Analog; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

Kits

In one aspect, the present invention provides a kit comprising a therapeutically effective amount of at least one 5'-Substituted Nucleoside Analog, or a pharmaceutically acceptable salt, solvate, ester or prodrug of said compound and a pharmaceutically acceptable carrier, vehicle or diluent.

In another aspect the present invention provides a kit comprising an amount of at least one 5'-Substituted Nucleoside Analog, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more 5'-Substituted Nucleoside Analogs and the one or more additional therapeutic agents are provided in the same container. In one embodiment, the one or more 5'-Substituted Nucleoside Analogs and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the structure:

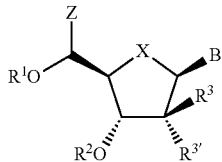

(I)

or a pharmaceutically acceptable salt thereof,
wherein:

X is O, S or $CH_2$;

Z is $C_1$-$C_6$ alkyl, $C_2$-$C_6$ alkenyl, $C_2$-$C_6$ alkynyl, —($C_1$-$C_3$ alkylene)$_m$-($C_3$-$C_7$ cycloalkyl), —($C_1$-$C_3$ alkylene)$_m$-$C_6$-$C_{10}$ aryl, —($C_1$-$C_3$ alkylene)$_m$-(4 to 7-membered heterocycloalkyl group), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —$N(R^{20})_2$, —$C(O)OR^{20}$, —$C(O)N(R^{20})_2$ and —$NHC(O)R^{20}$;

B is a natural or non-natural purine or pyrimidine base, or B is selected from one of the following groups:

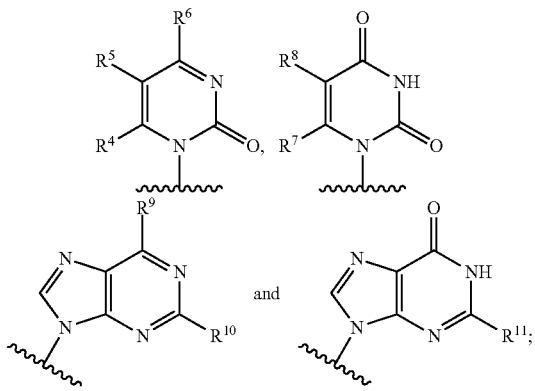

$R^1$ is H, —C(O)—$C_{1-6}$ alkyl,

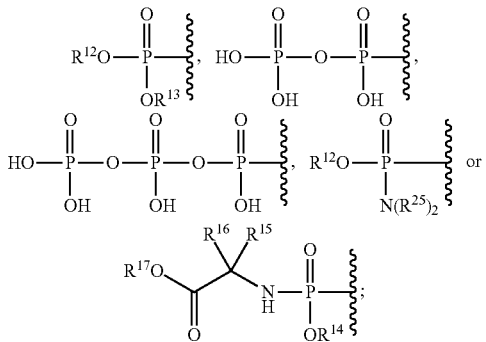

$R^2$ is H or —C(O)—$C_{1-6}$ alkyl, or $R^1$ and $R^2$ join to form a group having the formula:

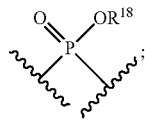

$R^3$ is halo, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl or $C_3$-$C_7$ cycloalkyl;

$R^{3'}$ is Cl, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl or $C_3$-$C_7$ cycloalkyl;

$R^4$, $R^5$, $R^7$ and $R^8$ are each independently H, $C_1$-$C_6$ alkyl, $C_1$-$C_6$ haloalkyl, $C_1$-$C_6$ hydroxyalkyl, halo, —$OR^{20}$, —$SR^{20}$ or —$N(R^{20})_2$;

$R^6$, $R^9$, $R^{10}$, $R^{11}$ are each independently selected from H, $C_1$-$C_6$ alkyl, $C_2$-$C_6$ alkenyl, $C_2$-$C_6$ alkynyl, $C_3$-$C_7$ cycloalkyl, 5- or 6-membered monocyclic heteroaryl, 9- or 10-membered bicyclic heteroaryl, halo, —$OR^{20}$, —$SR^{20}$, —$S(O)R^{20}$, —$S(O)_2R^{20}$, —$S(O)_2N(R^{20})_2$, —$NHC(O)OR^{20}$, —$NHC(O)N(R^{20})_2$, $C_1$-$C_6$ haloalkyl, $C_1$-$C_6$ hydroxyalkyl, —O—($C_1$-$C_6$ haloalkyl), —CN, —$NO_2$, —$N(R^{20})_2$, —$NH(C_1$-$C_6$ alkylene)-(5- or 6-membered monocyclic heteroaryl), —$NH(C_1$-$C_6$ alkylene)-(9- or 10-membered bicyclic heteroaryl), —$C(O)R^{20}$, —$C(O)OR^{20}$, —$C(O)N(R^{20})_2$ and —$NHC(O)R^{20}$, wherein said $C_2$-$C_6$ alkenyl group and said $C_2$-$C_6$ alkynyl group can be optionally substituted with a halo group;

$R^{12}$ is H or —($C_1$-$C_6$ alkylene)-T-$R^{21}$;

$R^{13}$ is H or —($C_1$-$C_6$ alkylene)-T-$R^{21}$, or $R^{12}$ and $R^{13}$ can join to form a $C_2$-$C_4$ alkylene group between the oxygen atoms that $R^{12}$ and $R^{13}$ are attached to, wherein said $C_2$-$C_4$ alkylene group is substituted with at least one $C_6$-$C_{10}$ aryl group;

$R^{14}$ is H, $C_6$-$C_{10}$ aryl, 5- or 6-membered monocyclic heteroaryl or 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with $R^{22}$;

$R^{15}$ is H, $C_1$-$C_6$ alkyl, $C_3$-$C_7$ cycloalkyl, phenyl or benzyl, wherein said $C_1$-$C_6$ alkyl can be optionally substituted with a group selected from halo, —$OR^{20}$, —$SR^{20}$, guanidino, —$N(R^{20})_2$, —$C(O)OR^{20}$, —$C(O)N(R^{20})_2$, —$NHC(O)R^{20}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —$OR^{20}$;

$R^{16}$ is H, $C_1$-$C_6$ alkyl, $C_3$-$C_7$ cycloalkyl, phenyl or benzyl, wherein said $C_1$-$C_6$ alkyl can be optionally substituted with a group selected from halo, —$OR^{20}$, —$SR^{20}$, guanidino, —$N(R_{20})_2$, —$C(O)OR^{20}$, —$C(O)N(R^{20})_2$, —$NHC(O)R^{20}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —$OR^{20}$;

$R^{17}$ is H, $C_1$-$C_{20}$ alkyl, $C_2$-$C_{20}$ alkenyl, —($C_1$-$C_3$ alkylene)$_m$-$C_3$-$C_7$ cycloalkyl, —($C_1$-$C_3$ alkylene)$_m$-$C_6$-$C_{10}$ aryl or adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —$OR^{20}$, —$C(O)OR^{20}$, CN, $NO_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —$N(R^{20})_2$, —$C(O)N(R^{20})_2$ —$SR^{20}$, —$S(O)R^{20}$, —$S(O)_2R^{20}$, —$S(O)_2N(R^{20})_2$, —$NHC(O)R^{20}$, —$NHC(O)OR^{20}$ and —$NHC(O)N(R^{20})_2$ and;

$R^{18}$ is H, $C_1$-$C_6$ alkyl, $C_3$-$C_7$ cycloalkyl, —$(C_1$-$C_3$ alkylene$)_m$-$C_6$-$C_{10}$ aryl, 5- or 6-membered monocyclic heteroaryl or 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —$N(R^{20})_2$, —$C(O)OR^{20}$, —$C(O)N(R^{20})_2$ and —$NHC(O)R^{20}$;

each occurrence of $R^{20}$ is independently H, $C_1$-$C_6$ alkyl, $C_1$-$C_6$ haloalkyl, $C_1$-$C_6$ hydroxyalkyl, —($C_1$-$C_3$ alkylene$)_m$, —($C_3$-$C_7$ cycloalkyl), —($C_1$-$C_3$ alkylene$)_m$-($C_6$-$C_{10}$ aryl), —($C_1$-$C_3$ alkylene$)_m$-(4 to 7-membered heterocycloalkyl), —($C_1$-$C_3$ alkylene$)_m$-(5- or 6-membered monocyclic heteroaryl) or —($C_1$-$C_3$ alkylene$)_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with $R^{26}$;

each occurrence of $R^{21}$ is independently H, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_7$ cycloalkyl, $C_3$-$C_7$ cycloalkenyl, 5- or 6-membered monocyclic heteroaryl, 9- or 10-membered bicyclic heteroaryl, —$OR^{20}$, —O—($C_1$-$C_6$ haloalkyl) or —$N(R^{20})_2$, wherein said $C_2$-$C_6$ alkenyl group, said $C_2$-$C_6$ alkynyl group, said $C_3$-$C_7$ cycloalkyl group, said $C_3$-$C_7$ cycloalkenyl group, said $C_6$-$C_{10}$ aryl group, said 5- or 6-membered monocyclic heteroaryl group or said 9- or 10-membered bicyclic heteroaryl group can be optionally substituted with up to five groups, each independently selected from $C_1$-$C_6$ alkyl, $C_2$-$C_6$ alkenyl, $C_2$-$C_6$ alkynyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —$N(R^{20})^2$, —$C(O)R^{20}$, —$C(O)OR^{20}$, —$C(O)N(R^{20})_2$ and —$NHC(O)R^{20}$;

$R^{22}$ represents from one to five substituent groups, each independently selected from $C_1$-$C_6$ alkyl, halo, —$OR^{20}$, —$SR^{20}$, $C_1$-$C_6$ haloalkyl, $C_1$-$C_6$ hydroxyalkyl, —O—($C_1$-$C_6$ haloalkyl), —CN, —$NO_2$, —$N(R^{20})_2$, —$C(O)OR^{20}$, —$C(O)N(R^{20})_2$ and —$NHC(O)R^{20}$, or any two $R^{22}$ groups on adjacent ring carbon atoms can combine to form —O—$R^{23}$—O—;

$R^{23}$ is —$[C(R^{24})_2]_n$—;

each occurrence of $R^{24}$ is independently H or $C_1$-$C_6$ alkyl;

each occurrence of $R^{25}$ is independently H, $C_1$-$C_6$ alkyl, $C_2$-$C_6$ alkenyl, $C_2$-$C_6$ alkynyl, $C_3$-$C_7$ cycloalkyl, —($C_1$-$C_3$ alkylene$)_m$-($C_6$-$C_{10}$ aryl), 4 to 7-membered heterocycloalkyl, 5- or 6-membered monocyclic heteroaryl or 9- or 10-membered bicyclic heteroaryl, wherein said $C_1$-$C_6$ alkyl group, said $C_2$-$C_6$ alkenyl group, said $C_2$-$C_6$ alkynyl group, said $C_3$-$C_7$ cycloalkyl group, said $C_6$-$C_{10}$ aryl group, said 4 to 7-membered heterocycloalkyl group, said -(5- or 6-membered monocyclic heteroaryl group or said 9- or 10-membered bicyclic heteroaryl group can be optionally substituted with $R^{26}$; or two $R^{25}$ groups, together with the common nitrogen atom to which they are attached, join to form a 4- to 7-membered heterocycloalkyl group;

$R^{26}$ represents from one to five substituent groups, each independently selected from $C_1$-$C_6$ alkyl, $C_2$-$C_6$ alkenyl, $C_2$-$C_6$ alkynyl, halo, —$OR^{27}$, —$SR^{27}$, $C_1$-$C_6$ haloalkyl, $C_1$-$C_6$ hydroxyalkyl, —O—($C_1$-$C_6$ haloalkyl), —CN, —$NO_2$, —$N(R^{27})_2$, —$C(O)OR^{27}$, —$C(O)N(R^{27})_2$ and —$NHC(O)R^{27}$;

each occurrence of $R^{27}$ is independently H, $C_1$-$C_6$ alkyl, $C_1$-$C_6$ haloalkyl, $C_1$-$C_6$ hydroxyalkyl, —($C_1$-$C_3$ alkylene$)_m$-($C_3$-$C_7$ cycloalkyl), —($C_1$-$C_3$ alkylene$)_m$-($C_6$-$C_{10}$ aryl), —($C_1$-$C_3$ alkylene)-(4 to 7-membered heterocycloalkyl), —($C_1$-$C_3$ alkylene$)_m$-(5- or 6-membered monocyclic heteroaryl) or —($C_1$-$C_3$ alkylene$)_m$-(9- or 10-membered bicyclic heteroaryl);

each occurrence of T is independently —S—, —O—, —SC(O)—, —SC(S)—, —OC(O)— and —OC(S)—;

each occurrence of m is independently 0 or 1; and each occurrence of n is independently 1 or 2.

2. The compound of claim 1, wherein X is O.

3. The compound of claim 1, wherein Z is $C_1$-$C_6$ alkyl.

4. The compound of claim 1, wherein $R^3$ is $C_{1-6}$ alkyl.

5. The compound of claim 1 having the formula (Ia):

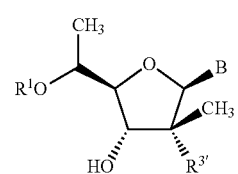

(Ia)

and pharmaceutically acceptable salts thereof, wherein:

B is:

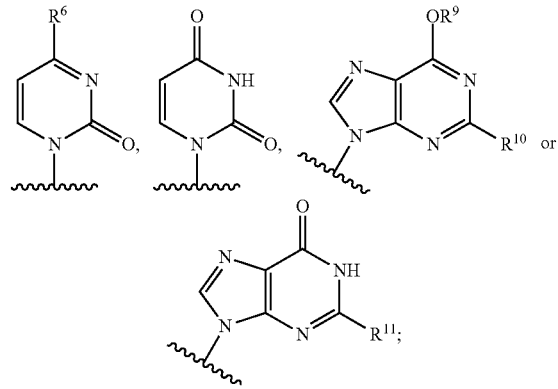

$R^{3'}$ is Cl;

$R^6$, $R^{16}$ and $R^{11}$ are each independently —$N(R^{20})_2$;

$R^9$ is —O—$CH_2$—($C_6$-$C_{10}$ aryl);

$R^{14}$ is $C_6$-$C_{10}$ aryl;

$R^{15}$ is $C_1$-$C_6$ alkyl; and $R^{17}$ is $C_1$-$C_6$ alkyl; and each occurrence of $R^{20}$ is independently H, —C(O)—($C_1$-$C_6$ alkyl) or —C(O)—($C_6$-$C_{10}$ aryl).

6. The compound of claim 5, wherein B is:

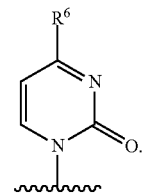

7. The compound of claim 5, wherein B is:

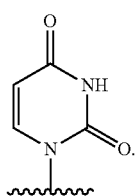 [SMILES: *n1ccc(=O)[nH]c1=O]

8. The compound of claim 5, wherein B is:

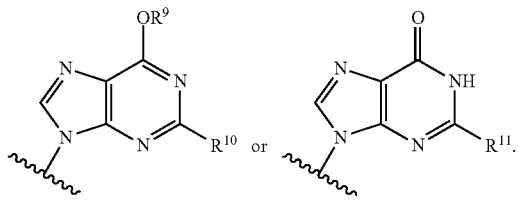

9. The compound of claim 5, wherein B is:

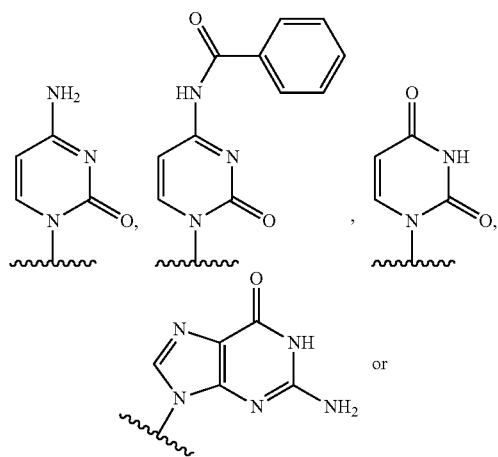

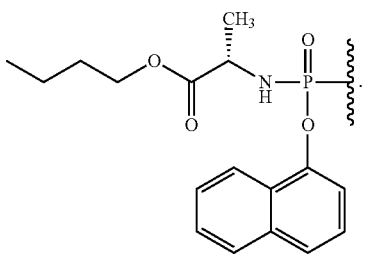 [SMILES: *P(=O)(N[C@@H](C)C(=O)OCCCC)Oc1cccc2ccccc12]

10. The compound of claim 5, wherein $R^1$ is H or

11. A pharmaceutical composition comprising an effective amount a compound of claim 1, or a pharmaceutically acceptable salt thereof, and a pharmaceutically acceptable carrier.

12. A method of treating a patient infected with HCV comprising administering an amount of a compound of claim 1, or a pharmaceutically acceptable salt thereof, effective to treat infection by HCV in said patient.

* * * * *